(12) United States Patent
Swezey

(10) Patent No.: US 10,485,487 B2
(45) Date of Patent: Nov. 26, 2019

(54) INFORMATION PROCESSING DEVICE, INFORMATION PROCESSING METHOD, AND INFORMATION PROCESSING PROGRAM

(71) Applicant: Rakuten, Inc., Tokyo (JP)

(72) Inventor: Robin Marcel Edwin Swezey, Tokyo (JP)

(73) Assignee: Rakuten, Inc., Tokyo (JP)

( * ) Notice: Subject to any disclaimer, the term of this patent is extended or adjusted under 35 U.S.C. 154(b) by 140 days.

(21) Appl. No.: 15/552,311

(22) PCT Filed: Feb. 20, 2015

(86) PCT No.: PCT/JP2015/054790
§ 371 (c)(1),
(2) Date: Aug. 21, 2017

(87) PCT Pub. No.: WO2016/132529
PCT Pub. Date: Aug. 25, 2016

(65) Prior Publication Data
US 2018/0035954 A1    Feb. 8, 2018

(51) Int. Cl.
*A61B 5/00*    (2006.01)
*A61B 5/01*    (2006.01)
*G01K 7/00*    (2006.01)
*A61B 10/00*   (2006.01)
*G16H 50/30*   (2018.01)
(Continued)

(52) U.S. Cl.
CPC .............. *A61B 5/7278* (2013.01); *A61B 5/01* (2013.01); *A61B 5/4306* (2013.01); *A61B 5/7275* (2013.01); *A61B 10/0012* (2013.01); *G01K 7/00* (2013.01); *G16H 10/60* (2018.01); *G16H 40/63* (2018.01); *G16H 40/67* (2018.01); *G16H 50/30* (2018.01); *G16H 50/50* (2018.01); *A61B 2010/0019* (2013.01); *G01K 13/002* (2013.01)

(58) Field of Classification Search
CPC .................................................. A61B 10/0012
USPC ............................................................ 702/131
See application file for complete search history.

(56) References Cited

U.S. PATENT DOCUMENTS 4,151,831 A * 5/1979 Lester ...................... A61B 5/01
                                                    368/10
4,752,880 A * 6/1988 Aeschlimann ..... A61B 10/0012
                                                    600/551
(Continued)

FOREIGN PATENT DOCUMENTS

JP           2009-45155 A       3/2009

*Primary Examiner* — Hien D Khuu
(74) *Attorney, Agent, or Firm* — Sughrue Mion, PLLC

(57) ABSTRACT

An information processing device determines a short term length and a long term length so that a timing(s) at which a short-term moving average of a plurality of days of body temperatures measured during past menstrual cycles falls below a long-term moving average of the body temperatures coincides with a menstrual date. The information processing device identifies the timing at which a short-term moving average calculated with the determined short term length exceeds a long-term moving average calculated with the determined long term length, of body temperatures measured during a target menstrual cycle. Based on the identified timing, the information processing device predicts the next menstrual date or estimates the arrival of an ovulation date.

6 Claims, 19 Drawing Sheets

(51) Int. Cl.
*G16H 40/63* (2018.01)
*G16H 40/67* (2018.01)
*G16H 10/60* (2018.01)
*G16H 50/50* (2018.01)
G01K 13/00 (2006.01)

(56) References Cited

U.S. PATENT DOCUMENTS

2016/0143630 A1* 5/2016 Pardey ............... A61B 10/0012
                                                            600/549
2018/0228474 A1* 8/2018 Suzuki ............... A61B 10/0012

* cited by examiner

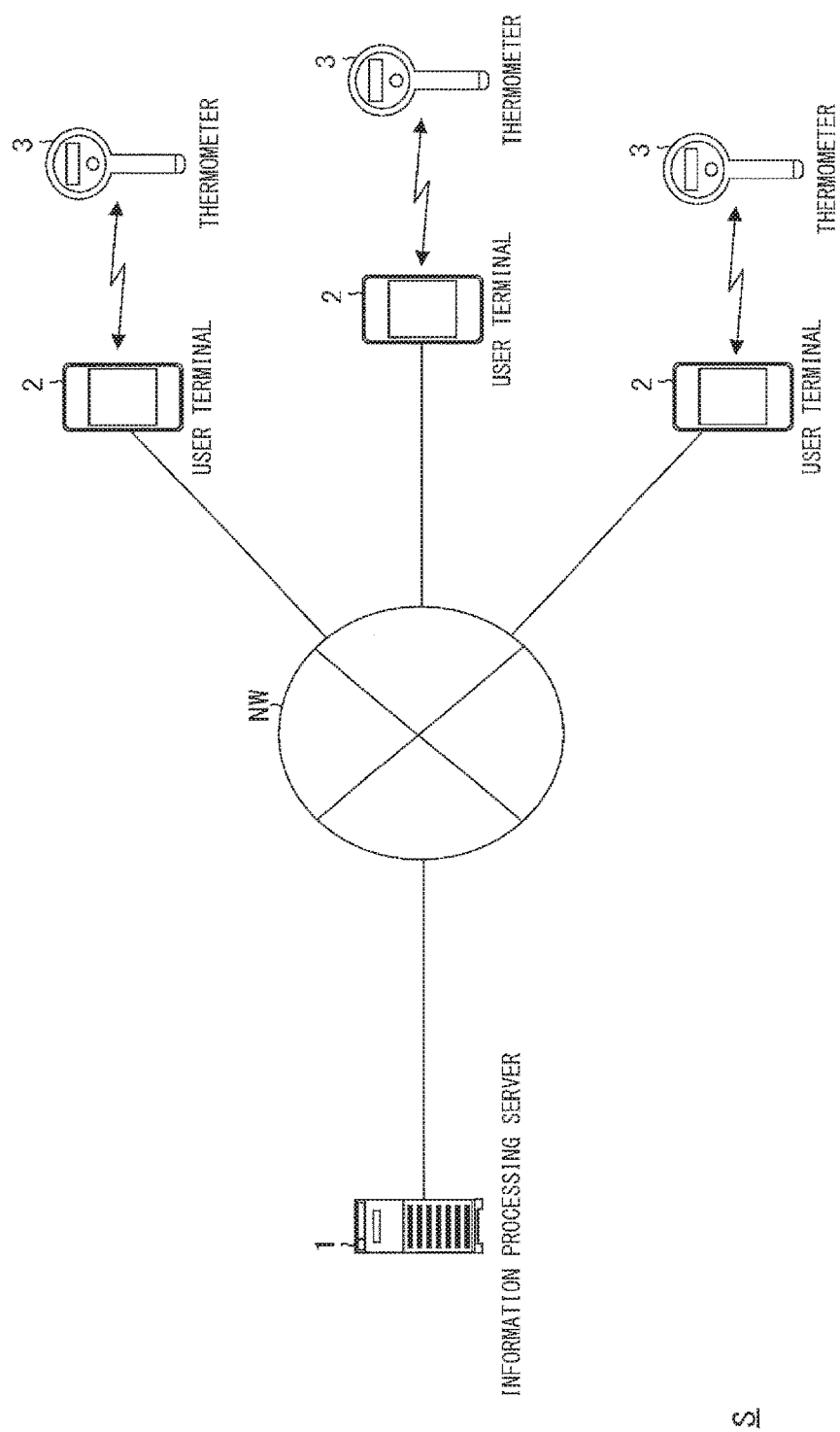

FIG.3

MEMBER INFORMATION DB — 12a

| USER ID |
| --- |
| PASSWORD |
| NICKNAME |
| NAME |
| BIRTH DATE |
| GENDER |
| ZIP CODE |
| ADDRESS |
| TELEPHONE NUMBER |
| EMAIL ADDRESS |
| . . . |

BODY TEMPERATURE DB — 12b

| USER ID |
| --- |
| MEASUREMENT DATE |
| MEASURED BODY TEMPERATURE |

MENSTRUAL DATE DB — 12c

| USER ID |
| --- |
| MENSTRUAL DATE |

PARAMETER DB — 12d

| USER ID |
| --- |
| REGISTRATION DATE |
| THRESHOLD VALUE FOR ABNORMAL VALUE REMOVAL |
| THRESHOLD VALUE FOR WINSORIZATION |
| REPRESENTATIVE VALUE TYPE |
| CYCLE-BASED PREDICTION METHOD?PREDICTED MENSTRUAL DATE |
| SHORT TERM LENGTH |
| LONG TERM LENGTH |
| ESTIMATED HIGH-TEMPERATURE PHASE LENGTH |

FIG.4A

CANDIDATE THRESHOLD VALUES OF FOR ABNORMAL VALUE REMOVAL $$\left\{ \begin{array}{c} 1\% \\ 5\% \\ 10\% \end{array} \right\}$$

×

CANDIDATE THRESHOLD VALUES WN FOR WINSORIZATION $$\left\{ \begin{array}{c} 5\% \\ 10\% \\ 15\% \end{array} \right\}$$

×

CANDIDATES PR FOR REPRESENTATIVE VALUE TYPE $$\left\{ \begin{array}{c} \text{AVERAGE VALUE} \\ \text{MEDIAN VALUE} \end{array} \right\}$$

FIG.4B

CANDIDATE COMBINATION CC1

| OF = 1% |
| WN = 5% |
| PR = AVERAGE VALUE |

CANDIDATE COMBINATION CC2

| OF = 5% |
| WN = 15% |
| PR = AVERAGE VALUE |

CANDIDATE COMBINATION CC3

| OF = 10% |
| WN = 10% |
| PR = MEDIAN VALU |

LATEST OF PASTS

| | 1ST | 2ND | 3RD | 4TH | 5TH | 6TH | 7TH | 8TH | 9TH |
|---|---|---|---|---|---|---|---|---|---|
| MENSTRUAL CYCLE | C1 30 DAYS | C2 35 DAYS | C3 24 DAYS | C4 34 DAYS | C5 29 DAYS | C6 29 DAYS | C7 29 DAYS | C8 30 DAYS | C9 32 DAYS |

FIRST SET  (C1)  | C2  C3  C4  C5  C6  C7 |

SECOND SET  (C2)  | C3  C4  C5  C6  C7  C8 |

THIRD SET  (C3)  | C4  C5  C6  C7  C8  C9 |

◯ BASE CYCLE    ▭ REFERENCE CYCLES

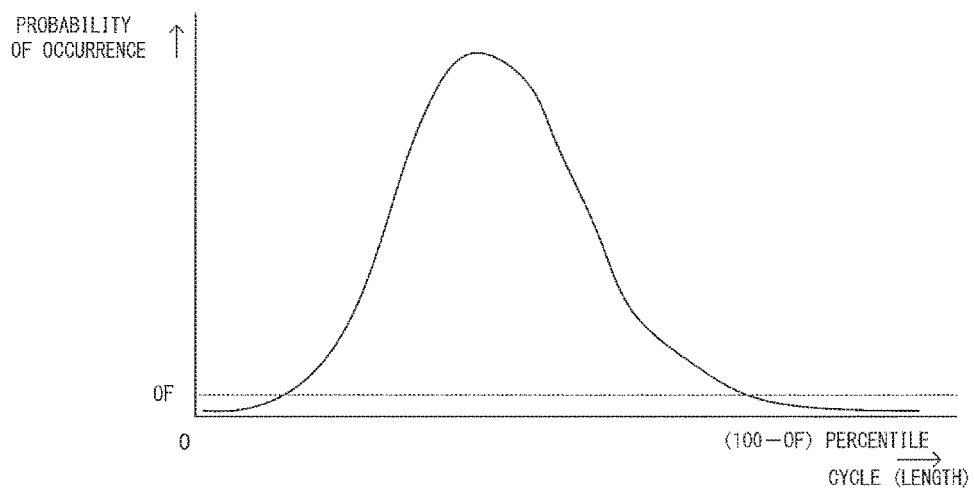
FIG.5A
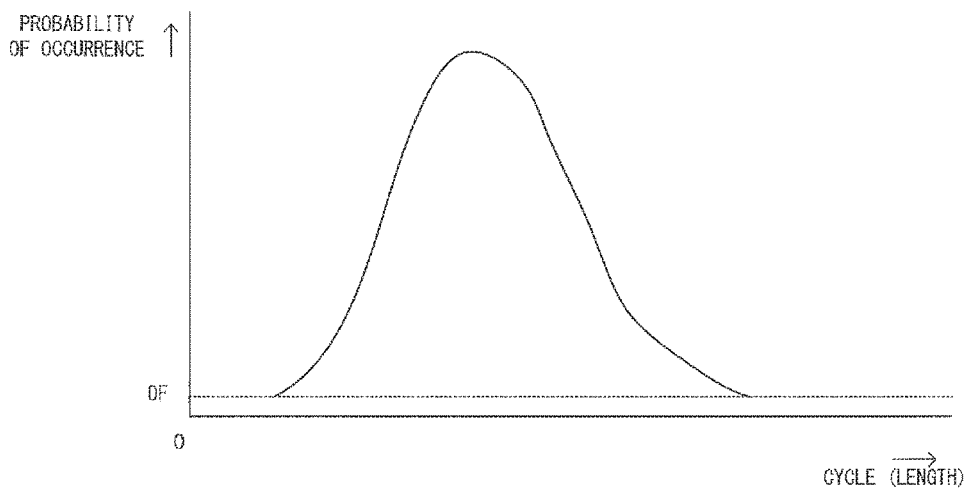
FIG.5B
FIG.5C

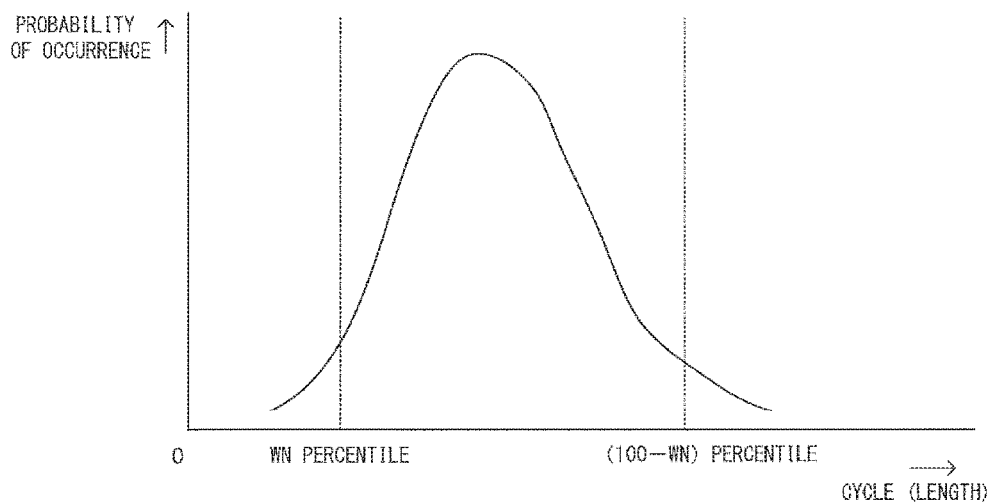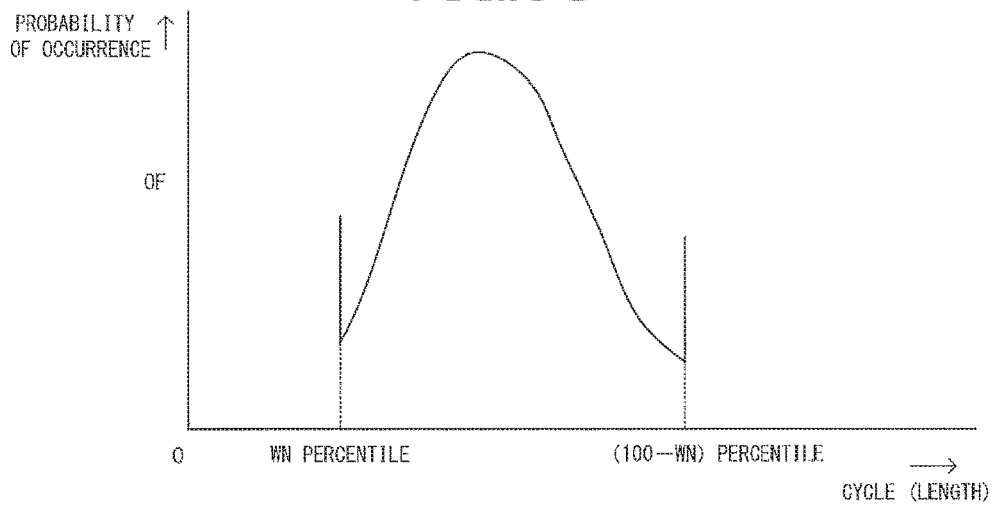

FIG.7A
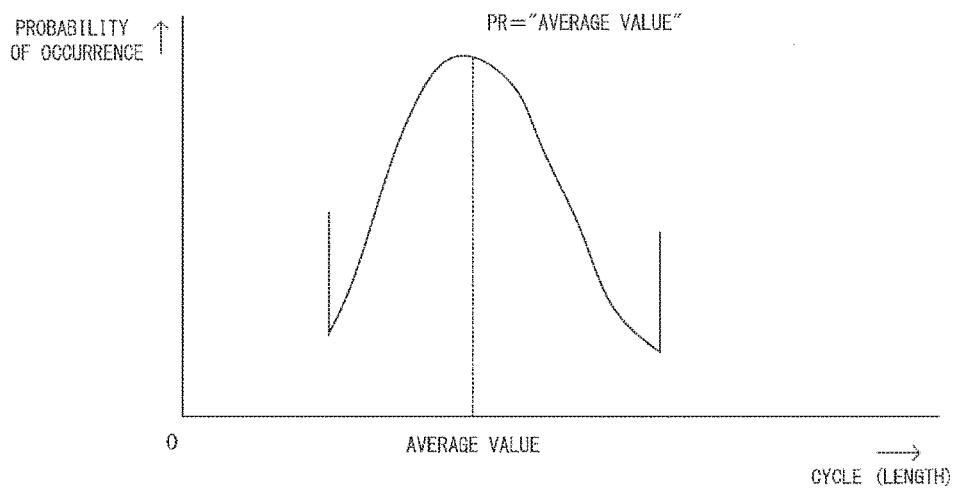
PR="AVERAGE VALUE"
PROBABILITY OF OCCURRENCE
0    AVERAGE VALUE    CYCLE (LENGTH)
FIG.7B
MODIFIED REFERENCE CYCLES
| C3 | C4 | C5 | C6 | C7 |
|---|---|---|---|---|
| 25 DAYS | 32 DAYS | 29 DAYS | 29 DAYS | 29 DAYS |
AVERAGE VALUE : 28.8 DAYS
DIFFERENCE BETWEEN BASE CYCLE LENGTH AND AVERAGE VALUE : | 30 − 28.8 | = 1.2

|  | FIRST SET | SECOND SET | THIRD SET | TOTAL |
|---|---|---|---|---|
| CANDIDATE COMBINATION CC1 | 1.2 DAYS × 1 | 0.5 DAY × 0.8 | 2.3 DAYS × 0.5 | 2.75 |
| CANDIDATE COMBINATION CC2 | 0.2 DAYS × 1 | 0.6 DAY × 0.8 | 1.5 DAYS × 0.5 | 1.43 |
| CANDIDATE COMBINATION CC3 | 1.5 DAYS × 1 | 0.6 DAY × 0.8 | 0.2 DAYS × 0.5 | 2.08 |

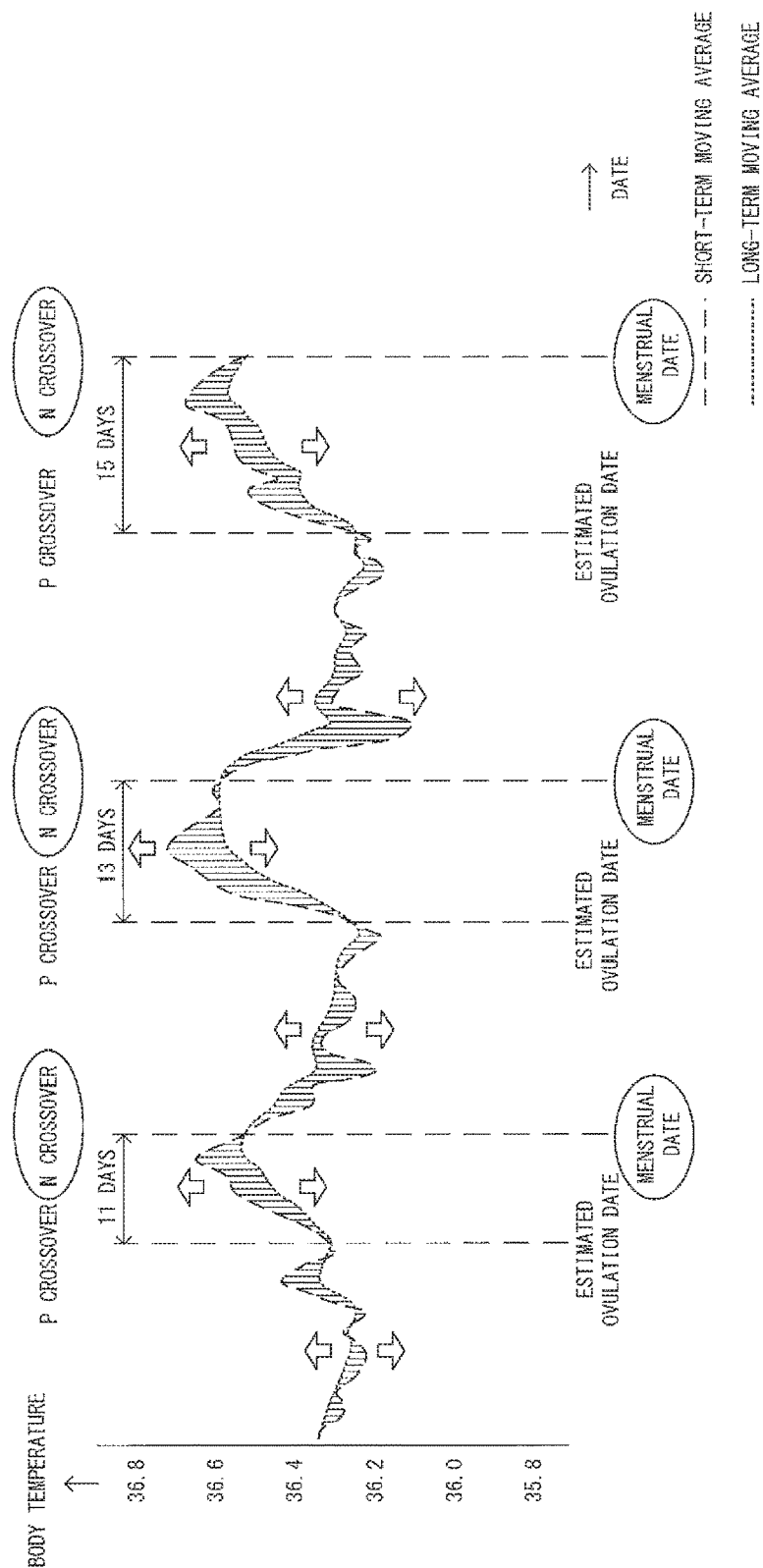

INFORMATION PROCESSING DEVICE, INFORMATION PROCESSING METHOD, AND INFORMATION PROCESSING PROGRAM

CROSS REFERENCE TO RELATED APPLICATIONS

This application is a National Stage of International Application No. PCT/JP2015/054790, filed on Feb. 20, 2015, the contents of all of which are incorporated herein by reference in their entirety.

TECHNICAL FIELD

The present invention relates to techniques for estimating an ovulation date or for predicting a menstrual date, based on measured body temperatures.

BACKGROUND ART

A menstrual cycle typically includes a low-temperature phase and a high-temperature phase, and the variability of high-temperature phase lengths is usually less than that of low-temperature phase lengths. Techniques using these characteristics are known in the art. For example, Patent Literature 1 discloses that if body temperature reaches or exceeds a reference body temperature for three consecutive days, a high-temperature phase is determined to start two days before the three consecutive days, that the day before the start date of the high-temperature phase is detected as an ovulation date, and that the next menstrual date is predicted by adding the average length of the high-temperature phase to the ovulation date.

CITATION LIST

Patent Literature

Patent Literature 1: JP 2009-45155 A

SUMMARY OF INVENTION

Technical Problem

Body temperature can fluctuate widely before and after the timing at which the transition from the low-temperature phase to the high-temperature phase actually occurs. Thus, if the body temperature reaches a high body temperature during the low-temperature phase, an estimation error can be caused by determining that the high-temperature phase starts when the body temperature reaches the high body temperature. On the other hand, as disclosed in Patent Literature 1, if it is determined that the high-temperature phase starts on the basis that the body temperature reaches the high temperature for a predetermined number of consecutive days, it is impossible to estimate a menstrual date and predict a menstrual date even after the transition to the high-temperature phase.

In view of the above, it is an object of the present invention to provide, for example, an information processing device and an information processing method that are capable of preventing a decrease in the accuracy of at least either estimating an ovulation date or predicting a menstrual date, even if body temperature fluctuates before and after the timing of the actual transition from a low-temperature phase to a high-temperature phase.

Solution to Problem

To solve the above problem, an aspect of some preferred embodiments includes an information processing device that includes determining means, identifying means, and estimating means. The determining means determines a short term length and a long term length so that timing(s) at which a moving average with the short term length falls below a moving average with the long term length, of a plurality of days of body temperatures measured during past one or more menstrual cycles, coincides with past one or more menstrual dates. The identifying means identifies a timing at which a moving average with the short term length determined by the determining means exceeds a moving average with the long term length determined by the determining means, of body temperatures measured during a target menstrual cycle. The estimating means predicts the next menstrual date during the target menstrual cycle or estimates the arrival of an ovulation date during the target menstrual cycle, based on the timing identified by the identifying means.

According to this invention, an information processing device determines a short term length and a long term length so that a timing at which a short-term moving average of body temperatures falls below a corresponding long-term moving average coincides with a menstrual date on which a low-temperature phase is considered to start. Based on short-term and long-term moving averages of body temperatures during the current menstrual cycle that are calculated using the determined lengths, the information processing device identifies a timing at which the short-term moving average exceeds the long-term moving average. The moving averages smooth time-series body temperature. Thus, by identifying this timing, even if the body temperature fluctuates before and after the timing of the actual transition from a low-temperature phase to a high-temperature phase, the timing can be correctly identified. A menstrual date comes at the timing of the transition from a low-temperature phase to a subsequent high-temperature phase. Thus, the information processing device can appropriately determine a short term length and a long term length. This can prevent a decrease in the accuracy of at least either estimating an ovulation date or predicting a menstrual date.

Another aspect of some preferred embodiments includes an estimating means that predicts the next menstrual date by adding a representative value of the numbers of days each between a timing at which the moving average with the short term length exceeds the moving average with the long term length and a timing at which the moving average with the short term length falls below the moving average with the long term length, during the past one or more menstrual cycles, to the timing identified by the identifying means.

The information processing device identifies the number of days between a timing at which the short-term moving average exceeds the long-term moving average and a timing at which the short-term moving average falls below the long-term moving average. The number of the days corresponds to the length of a target user's high-temperature phase. Thus, the information processing device can perform at least either estimation of her ovulation date or prediction of her menstrual date, more appropriately based on how long the target woman's high-temperature phase tends to last.

Another aspect of some preferred embodiments includes an information processing device in which the determining means determines the short term length and the long term length so that the time difference between a menstrual date and a timing at which a short-term moving average of body temperatures measured during the past one or more menstrual cycles falls below a long-term moving average of the body temperatures is small, and also so that the value of integral of the difference between the short-term moving average and the long-term moving average across the past one or more menstrual cycles is large.

The larger the value of integral of the difference between the short-term and the long-term moving averages of the body temperatures is, the more appropriately the information processing device can identify a timing at which the short-term moving average exceeds the long-term moving average. This invention enables the information processing device to determine more appropriate short and long term lengths, based on this integral and the time difference between a menstrual date and a timing at which the short-term moving average of the body temperatures falls below the long-term moving average.

Another aspect of some preferred embodiments includes an information processing device further including predicting means. If the identifying means does not identify a timing at which the moving average with the short term length exceeds the moving average with the long term length, the predicting means predicts the next menstrual date, based on the lengths of the past one or more menstrual cycles.

This enables the information processing device to predict her menstrual date, even when the transition from a low-temperature phase to a high-temperature phase has not yet occurred.

Another aspect of some preferred embodiments includes an information processing method performed by a computer. The method includes the following steps. A short term length and a long term length are determined so that timing(s) at which a moving average with the short term length falls below a moving average with the long term length, of a plurality of days of body temperatures measured during past one or more menstrual cycles, coincides with past one or more menstrual dates. A timing at which a moving average with the determined short term length exceeds a moving average with the determined long term length, of body temperatures measured during a target menstrual cycle, is identified. Based on the identified timing, the next menstrual date during the target menstrual cycle is predicted or the arrival of an ovulation date during the target menstrual cycle is estimated.

Another aspect of some preferred embodiments includes programming that causes a computer to function as determining means, identifying means, and estimating means. The determining means determines a short term length and a long term length so that timing (s) at which a moving average with the short term length falls below a moving average with the long term length, of a plurality of days of body temperatures measured during past one or more menstrual cycles, coincides with past one or more menstrual dates. The identifying means identifies a timing at which a moving average with the short term length determined by the determining means exceeds a moving average with the long term length determined by the determining means, of body temperatures measured during a target menstrual cycle. The estimating means predicts the next menstrual date during the target menstrual cycle or estimates the arrival of an ovulation date during the target menstrual cycle, based on the timing identified by the identifying means.

Advantageous Effects of Invention

An information processing device determines a short term length and a long term length so that a timing at which a short-term moving average of body temperatures falls below a corresponding long-term moving average coincides with a menstrual date on which a low-temperature phase is considered to start. Based on short-term and long-term moving averages of body temperatures during the current menstrual cycle that are calculated using the determined lengths, the information processing device identifies a timing at which the short-term moving average exceeds the long-term moving average. The moving averages smooth time-series body temperature. Thus, by identifying this timing, even if the body temperature fluctuates before and after the timing of the actual transition from a low-temperature phase to a high-temperature phase, the timing can be correctly identified. A menstrual date comes at the timing of the transition from a low-temperature phase to a subsequent high-temperature phase. Thus, the information processing device can appropriately determine a short term length and a long term length. This can prevent a decrease in the accuracy of at least either estimating an ovulation date or predicting a menstrual date.

BRIEF DESCRIPTION OF DRAWINGS

FIG. 1 is a diagram schematically showing an example configuration of an information processing system S according to an embodiment.

FIG. 3 is a diagram showing example entries in databases created in a storage unit 12 of the information processing server 1.

FIG. 4A is a diagram showing an example of candidate parameters.

FIG. 4B is a diagram showing three of a plurality of generated candidate combinations as an example.

FIG. 4C is a diagram showing an example of obtaining cycle sets.

FIG. 5A is a graph showing an example of the frequency distribution of reference cycles obtained by a modified reference cycle obtainer 143 and also showing an example of the positional relationship between the frequency distribution and a threshold value OF.

FIG. 5B is a diagram showing, as an example, the reference cycles from among which an abnormal value has been removed.

FIG. 5C is a graph showing an example of the frequency distribution of the reference cycles left after removal of the abnormal value.

FIG. 6A is a graph showing an example of the frequency distribution of the reference cycles left after removal of the abnormal value and also showing an example of the positional relationship between the frequency distribution and a threshold value WN.

FIG. 6B is a diagram showing, as an example, the reference cycles to which winsorization has been applied.

FIG. 6C is a graph showing an example of the frequency distribution of the winsorized reference cycles.

FIG. 7A is a graph showing an example of the frequency distribution of the winsorized reference cycles and also showing an example of the positional relationship between the frequency distribution and a representative value.

FIG. 7B is a diagram illustrating an example of how the representative value is determined and how the difference between the representative value and the length of a base cycle is determined.

FIG. 11 is a diagram showing an example of the relationship between the short-term moving average line of the body temperatures and the long-term moving average line of the body temperatures during the past three menstrual cycles.

DESCRIPTION OF EMBODIMENTS

Figure 2A:
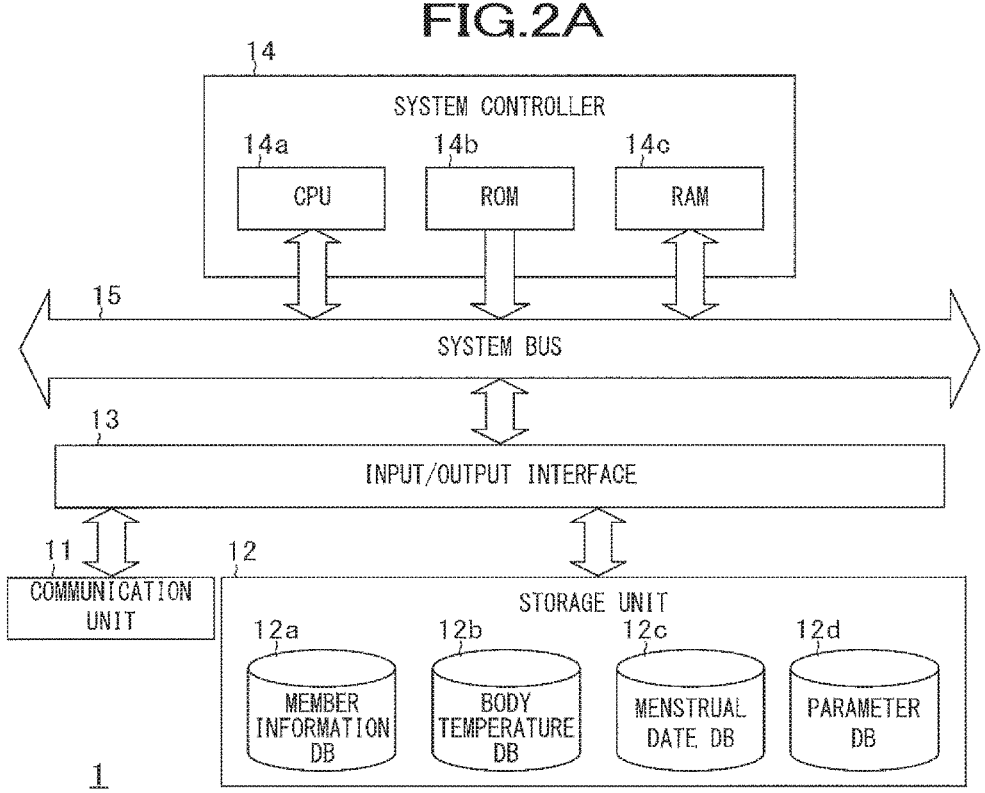
FIG. 2A is a block diagram schematically showing an example configuration of an information processing server 1 according to an embodiment.

The following describes an embodiment of the present invention in detail with reference to the drawings. The embodiment described below is an embodiment in which the present invention is applied to an information processing system.

1. Configuration and Functional Overview of Information Processing System

First, a configuration and a functional overview of an information processing system S according to this embodiment are described with reference to FIG. 1. FIG. 1 is a diagram schematically showing an example configuration of the information processing system S according to this embodiment.

As shown in FIG. 1, the information processing system S includes an information processing server 1, a plurality of user terminals 2, and a plurality of thermometers 3. The information processing server 1 is capable of exchanging data with each user terminal 2 over a network NW, for example, using TCP/IP as a communication protocol. The network NW includes, for example, the Internet, a dedicated communication line (e.g., community antenna television (CATV) line), a mobile communication network (including base stations), and a gateway.

The information processing server 1 is a server device that delivers information about woman's health to each user terminal 2. The information processing server 1 obtains, from the user terminal 2, information including a corresponding user's basal body temperatures and menstrual dates. The information processing server 1 then estimates the user's ovulation date or predicts the next menstrual date, based on the obtained information.

Each user terminal 2 is a terminal device of a user who uses the information processing system S. The user terminal 2 may be, for example, a smartphone, a tablet computer, a personal digital assistant (PDA), a mobile phone, or a personal computer. The user terminal 2 sends basal body temperatures measured by a corresponding thermometer 3 to the information processing server 1. The user terminal 2 also sends actual menstrual dates entered by the user to the information processing server 1. The user terminal 2 then displays information including an ovulation date and a menstrual date that are estimated by the information processing server 1.

The thermometer 3 is a digital thermometer that measures the user's basal body temperature. The thermometer 3 sends the measured body temperature to the user terminal 2, for example, via near field communication. The user may manually enter her body temperature measured by the thermometer into the user terminal 2.

The user takes her body temperature with the thermometer 3, for example, on a daily basis (once a day). An actually measured body temperature is referred to as an actual measurement. When the user enters an actual menstrual date, a menstrual cycle is determined. The menstrual cycle is, for example, the period from the preceding menstrual date to the day before the next menstrual date. When menstruation lasts two or more days, the information processing server 1 determines the first day of the menstruation to be a menstrual date used to identify the menstrual cycle. The information processing server 1 uses a cycle-based prediction method and a temperature-based prediction method to predict the next menstrual date. The cycle-based prediction method is a method using the lengths of a plurality of past menstrual cycles. The temperature-based prediction method is a method using actually measured body temperatures. When using the temperature-based prediction method, the information processing server 1 may predict the next menstrual date and also estimate an ovulation date during the current menstrual cycle. The current menstrual cycle is the menstrual cycle that starts on the last of the past menstrual dates and ends on the day before the next menstrual date. That is, the current menstrual cycle is the menstrual cycle that is continuing.

2. Configuration of Information Processing Server

The following describes a configuration of the information processing server 1 with reference to FIGS. 2A to 3.

FIG. 2A is a block diagram schematically showing an example configuration of the information processing server 1 according to this embodiment. As shown in FIG. 2A, the information processing server 1 includes a communication unit 11, a storage unit 12, an input/output interface 13, and a system controller 14. The system controller 14 and the input/output interface 13 are connected via a system bus 15.

The communication unit 11 connects to the network NW and controls the state of communications with, for example, the user terminals 2.

The storage unit 12 includes, for example, hard disk drives. The storage unit 12 is an example of storage means. In this storage unit 12, a member information DB 12, a body temperature DB 12b, a menstrual date DB 12c, a parameter DB 12d, and other databases are created. "DB" is an abbreviation for database. FIG. 3 is a diagram showing example entries in databases created in a storage unit 12 of the information processing server 1.

The member information DB 12a stores, for each user who uses the information processing system S, user information about the user. Specifically, the member information DB 12a stores, as the user information, the user's user ID, password, nickname, name, birth date, gender, zip code, address, telephone number, email address, and other user attributes in association with each other. The user ID is identification information of the user.

The body temperature DB 12b stores information about actual measurements. Specifically, the body temperature DB 12b stores a user ID, a measurement date, and an actual measurement in association with each other. The user ID indicates a user who took her body temperature. The measurement date indicates the date on which the body temperature was measured. For example, the system controller 14 receives, from a user terminal 2, a user ID of a user that uses the user terminal 2, a measurement date, and an actual measurement. Subsequently, the system controller 14 stores the received information in the body temperature DB 12b.

The menstrual date DB 12c stores information about menstrual dates. Specifically, the menstrual date DB 12c stores a user ID and a menstrual date in association with each other. The user ID indicates the user who entered the menstrual date. For example, the system controller 14 receives, from a user terminal 2, a user ID of a user that uses the user terminal 2 and a menstrual date that a user entered. Subsequently, the system controller 14 stores the received information in the menstrual date DB 12c.

The parameter DB 12d stores parameter information including parameters used to predict a menstrual date. Basically each time a user's new menstrual cycle starts, the system controller 14 stores parameter information in the parameter DB 12d. Specifically, the parameter DB 12d stores, as parameter information, a user ID, a registration date, parameters for the cycle-based prediction method, a cycle-based prediction method-predicted menstrual date, parameters for temperature-based prediction method, and an estimated high-temperature phase length in association with each other. The user ID indicates a user whose menstrual date is predicted by the parameters. The registration date indicates the date on which the parameter information was stored in the parameter DB 12d. The parameters for the cycle-based prediction method include, for example, a threshold value for abnormal value removal, a threshold value for winsorization (winsorizing), and a representative value type. Abnormal value removal means removing, from a plurality of menstrual cycles, data that exceeds a threshold value or is outside the threshold value as an outlier. This outlier is referred to as an abnormal value. The abnormal value is an example of a first outlier of the present invention. The threshold value for abnormal value removal indicates a threshold value for a menstrual cycle to be removed as an abnormal values. Specifically, the threshold value for abnormal value removal may include, for example, a percentage. The threshold value for abnormal value removal is an example of a first threshold value of the present invention. Winsorization means changing the value of data that exceeds a threshold value or is outside the threshold value as an outlier, in the distribution of threshold value, to the threshold value. This outlier is an example of a second outlier of the present invention. The threshold value for winsorization in this embodiment indicates a threshold value for a menstrual cycle to be changed in length among a plurality of menstrual cycles and also indicates the length after the change. Specifically, the threshold value for winsorization may include, for example, a percentage. The threshold value for winsorization is an example of a second threshold value of the present invention. The representative value type indicates how to obtain a representative value of a plurality of menstrual cycles. Specifically, the representative value type indicates whether to obtain the average value or the median value. The cycle-based prediction method-predicted menstrual date is a menstrual date predicted by the cycle-based prediction method. The parameters for temperature-based prediction method include, for example, a short term length and a long term length. The short term length is the number of days used to calculate a short-term moving average of body temperatures. The long term length is the number of days used to calculate a long-term moving average of body temperatures. The long term length is longer than the short term length. The estimated high-temperature phase length is the length of a high-temperature phase estimated by the temperature-based prediction method. Each menstrual cycle can be typically divided into a low-temperature phase and a high-temperature phase. The low-temperature phase is a period in which body temperature is relatively low during the menstrual cycle. The high-temperature phase is a period in which body temperature is relatively high during the menstrual cycle. As soon as the menstrual cycle starts, the low-temperature phase starts and then transitions to the high-temperature phase.

The following describes other information stored in the storage unit 12. The storage unit 12 stores various data for displaying web pages, such as HTML documents, extensible markup language (XML) documents, image data, text data, and electronic documents. The storage unit 12 also stores various set values, threshold values, constants, and the like.

The storage unit 12 also stores various programs, such as an operating system, a World Wide Web (WWW) server program, a database management system (DBMS), and a prediction processing program. The prediction processing program is a program for estimating an ovulation date and for predicting a menstrual date. The prediction processing program is an example of an information processing program according to the present invention. The various programs may be available from, for example, another server device over the network NW. Alternatively, the various programs may be recorded in a recording medium, such as a magnetic tape, an optical disk, or a memory card, and be read via a drive device. The prediction processing program may be a program product.

The storage unit 12 also stores a terminal application program. The terminal application program is a program to be performed by each user terminal 2. The terminal application program is a program for sending information including actual measurements and menstrual dates to the information processing server 1 and for displaying information including an estimated ovulation date and a predicted menstrual date. The user terminal 2 downloads the terminal application program, for example, from the information processing server 1.

The input/output interface 13 performs interface processing between the communication unit 11 and the storage unit 12, and the system controller 14.

The system controller 14 includes, for example, a CPU 14a, a read only memory (ROM) 14b, and a random access memory (RAM) 14c. The CPU 14a is an example processor. The present invention can also be applied to various processors that differ from CPUs. The storage unit 12, the ROM 14b, and the RAM 14c are each an example memory. The present invention can also be applied to various memories that differ from hard disks, ROMs, and RAMs.

The information processing server 1 may include a plurality of server devices. For example, a server device that obtains information from the user terminals 2, a server device that estimates an ovulation date and predicts a menstrual date, a server device that provides information to the user terminals 2, a server device that manages databases, and other server devices may be connected to each other via a LAN or the like. In this case, the server device that estimates an ovulation date and predicts a menstrual date may be an example of an information processing device according to the present invention. The information processing device according to the present invention may be implemented on a single server device or may be implemented on a plurality of server devices that cooperate with each other in processing.

3. Functional Overview of System Controller

Figure 2B:
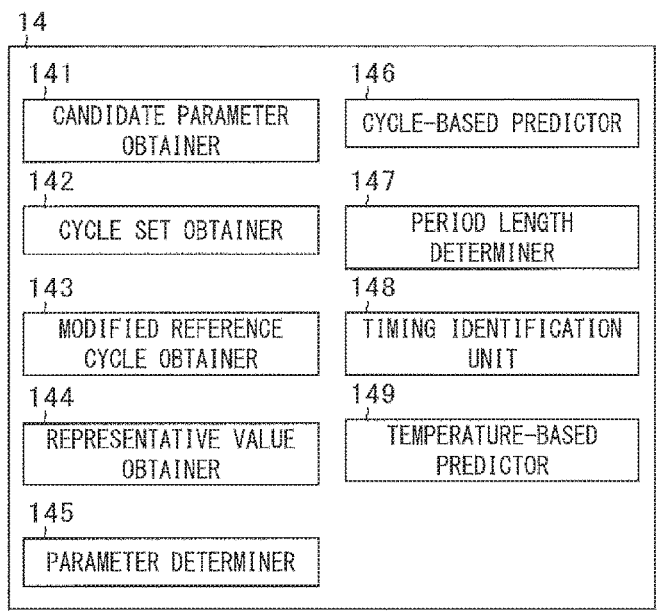
FIG. 2B is a diagram showing example functional blocks of a system controller 14 according to an embodiment.

The following describes a functional overview of the system controller 14 with reference to FIG. 2B and FIGS. 4A to 12B. FIG. 2B is a diagram showing example functional blocks of the system controller 14 according to this embodiment. The system controller 14 determines whether to use the cycle-based prediction method or the temperature-based prediction method, based on a predetermined criterion. The system controller 14 then predicts the next menstrual date using the determined method. To this end, as shown in FIG. 2B, the prediction processing program and other programs, which are read and executed by the CPU 14a, cause the system controller 14 to function as, for example, a candidate parameter obtainer 141, a cycle set obtainer 142, a modified reference cycle obtainer 143, a representative value obtainer 144, a parameter determiner 145, a cycle-based predictor 146, a period length determiner 147, a timing identification unit 148, and a temperature-based predictor 149. The cycle-based predictor 146 is an example of predicting means of the present invention. The period length determiner 147 is an example of determining means of the present invention. The timing identification unit 148 is an example of identifying means of the present invention. The temperature-based predictor 149 is an example of estimating means of the present invention.

3-1. Cycle-Based Prediction Method

When using the cycle-based prediction method, the system controller 14 obtains a plurality of past menstrual cycles. The system controller 14 then applies predetermined processing to an outlier identified from the past menstrual cycles, based on a threshold value, to obtain a plurality of modified menstrual cycles. The predetermined processing may be, for example, to remove the outlier identified based on the threshold value or to winsorize the outlier identified based on the threshold value. Alternatively, the predetermined processing may be for the system controller 14 to perform both the abnormal value removal and the winsorization. In this case, the system controller 14 may first perform the abnormal value removal and then perform the winsorization. Even after an abnormal value is removed from the plurality of menstrual cycles, there may be still a large variation in length among menstrual cycles. The large variation can reduce the accuracy of the prediction. However, simple removal of another outlier further identified after removal of the abnormal value may reduce the accuracy of the prediction. For this reason, winsorization to change the outlier so as to leave information indicating that the outlier is outside the distribution of the menstrual cycles can prevent a decrease in the accuracy of the prediction. After the plurality of menstrual cycles are modified, the system controller 14 calculates a representative value of the modified menstrual cycles. The system controller 14 then predicts the next menstrual date, based on the representative value of the menstrual cycles.

3-1-1. Determination of Parameters

In order to predict a menstrual date using the cycle-based prediction method, the system controller 14 determines, for each user, parameters used in the cycle-based prediction method. The determined parameters include at least one of a threshold value for abnormal value removal, a threshold value for winsorization, and a representative value type. At least one of the threshold value for abnormal value removal, the threshold value for winsorization, and the representative value type may be predetermined, for example, in the whole information processing system S. For example, when only the abnormal value removal is used to modify a plurality of menstrual cycles, the threshold value for winsorization is not required. Alternatively, for example, when only the winsorization is used to modify a plurality of menstrual cycles, the threshold value for abnormal value removal is not required.

The system controller 14 predicts a menstrual cycle by the cycle-based prediction method, using a plurality of past menstrual cycles and candidate parameters. The system controller 14 then compares the predicted menstrual cycle with another past menstrual cycle to determine which of the candidate parameters to use as parameters for actual prediction. The system controller 14 uses the determined parameters and thus can accurately predict the next menstrual date, even if there is variation in length among the plurality of past menstrual cycles.

The candidate parameter obtainer 141 obtains a plurality of candidate threshold values for an outlier. Specifically, the candidate parameter obtainer 141 obtains at least either a plurality of candidate threshold values for abnormal value removal or a plurality of candidate threshold values for winsorization. For example, the storage unit 12 may store a table including a plurality of candidate threshold values for abnormal value removal. Also for example, the storage unit 12 may store a table including a plurality of candidate threshold values for winsorization. The candidate parameter obtainer 141 may obtain a plurality of candidate threshold values from the table stored in the storage unit 12. The number of the candidates for each threshold value is two or more. The number of the candidate threshold values for abnormal value removal may or may not be the same as the number of candidates for threshold value for winsorization. When the representative value type is not predetermined in the whole information processing system S, the candidate parameter obtainer 141 may obtain "average value" and "median value" as candidates for the representative value type. For example, if the distribution of the menstrual cycles has a central tendency or has symmetry, use of the average can improve the accuracy of the prediction. On the other hand, if the distribution of the menstrual cycles does not have a central tendency or does not have symmetry, use of the median value can improve the accuracy of the prediction. FIG. 4A is a diagram showing an example of the candidate parameters. In the example of FIG. 4A, the number of the candidate threshold values for abnormal value removal is three, and the number of candidate threshold values for winsorization is three. "Average value" and "median value" are candidates for the representative value type.

If two or more parameters are determined from among the threshold value for abnormal value removal, the threshold value for winsorization, and the representative value type, the candidate parameter obtainer 141 generates a plurality of combinations of two or more candidate parameters. These combinations are referred to as candidate combinations. For example, when three parameters are determined, the candidate parameter obtainer 141 generates a plurality of candidate combinations each including one of the candidate threshold values for abnormal value removal, one of the candidate threshold values for winsorization, and one of the candidates for the representative value type. FIG. 4B is a diagram showing three of the plurality of generated candidate combinations as an example. In the example of FIG. 4A, eighteen candidate combinations can be generated.

The cycle set obtainer 142 obtains a cycle set including one base cycle and reference cycles, from among a plurality of past menstrual cycles of a target woman whose menstrual date is to be predicted. The reference cycles are menstrual cycles used to provisionally predict a menstrual cycle. The base cycle is a menstrual cycle to be compared with the provisionally predicted menstrual cycle. The base cycle may be one of the reference cycles. Alternatively, the base cycle may be a menstrual cycle different from any of the reference cycles. The reference cycles may or may not be continuous. The base cycle may or may not be continuous with the reference cycles. The temporal position of the base cycle may be earlier or later than the temporal positions of the reference cycles. The base cycle may be sandwiched between the reference cycles.

The cycle set obtainer 142 may obtain only one cycle set or may obtain a plurality of cycle sets. The number of cycle sets may be preset by an administrator of the information processing system S or may be determined by the cycle set obtainer 142. When obtaining a plurality of cycle sets, the cycle set obtainer 142 may obtain a plurality of cycle sets among which at least one of the following is different: for example, the temporal position of a base cycle, some or all of a plurality of reference cycles, and the number of reference cycles. FIG. 4C is a diagram showing an example of obtaining cycle sets. In FIG. 4C, numbers above past menstrual cycles C1 to C9 indicate the temporal positions of the menstrual cycles. The sign Cn has a suffix number n that indicates the corresponding temporal position. For example, the first menstrual cycle C1 is the latest of the past menstrual cycles and the second menstrual cycle C2 is the second latest menstrual cycle. In the example of FIG. 4C, the number of reference cycles in each cycle set is six. The six reference cycles are continuous. The base cycle is continuous with the six reference cycles and newer than these reference cycles. In the example of FIG. 4C, three cycle sets have been obtained. For example, the first cycle set includes a base cycle C1 and reference cycles C2 to C7. The second cycle set includes a base cycle C2 and reference cycles C3 to C8. The third cycle set includes a base cycle C3 and reference cycles C4 to C9.

The modified reference cycle obtainer 143 modifies, for each candidate threshold value obtained by the candidate parameter obtainer 141, the reference cycles included in the cycle set obtained by the cycle set obtainer 142 using the candidate threshold value. The cycle set obtainer 142 then obtains the modified reference cycles. When the candidate parameter obtainer 141 obtains candidate combinations each including at least a threshold value for abnormal value removal and a threshold value for winsorization, the modified reference cycle obtainer 143 modifies, for each candidate combination, the reference cycles and then obtains the modified reference cycles.

For example, assume that the candidate parameter obtainer 141 obtains at least a candidate threshold value OF for abnormal value removal as a candidate threshold value. In this case, the cycle set obtainer 142 calculates, for each length, the probability of occurrence of a reference cycle having the length. The cycle set obtainer 142 then removes, from among the reference cycles, a reference cycle having a length whose probability of occurrence is less than OF % as an abnormal value. The cycle set obtainer 142 then obtains, as modified reference cycles, the reference cycles left after removal of the abnormal value.

For example, assume that the candidate parameter obtainer 141 obtains at least a candidate threshold value WN for winsorization as a candidate threshold value. In this case, the cycle set obtainer 142 changes the length of a reference cycle having a length below the WN-th percentile, among the reference cycles arranged in ascending order of length, to be at the WN-th percentile. The cycle set obtainer 142 further changes, from among the reference cycles, the length of a reference cycle having a length above the (100−WN)-th percentile to be at the (100−WN)-th percentile. In some cases, the reference cycles before the modification include no reference cycle at the position absolutely identical to the position indicated by the threshold value WN. For example, when the number of reference cycles is six, a reference cycle is at a position of 16.7% and another reference cycle is at a position of 33.3%. However, when the threshold value WN is 20%, there is no reference cycle at a position of 20%. In this case, the modified reference cycle obtainer 143 may calculate the WN-the percentile by interpolation, for example, based on the length and the position of a reference cycle immediately before the position indicated by the threshold value WN and on the length and the position of a reference cycle immediately after the position indicated by the threshold value WN. Alternatively, for example, the modified reference cycle obtainer 143 may change the length of a reference cycle having a length below the WN-th percentile to the length of the latest of reference cycles that are inside the position indicated by the threshold value WN. "Inside" means the range from the WN-th percentile WN to the (100−WN)-th percentile. The same as described for the WN-th percentile may apply to a case where there is no reference cycle at the position absolutely identical to the position indicated by the threshold value (100−WN).

For example, when the candidate parameter obtainer 141 obtains, as candidate threshold values, a candidate combination including both the candidate threshold value OF for abnormal value removal and the candidate threshold value WN for winsorization, the modified reference cycle obtainer 143 may first perform abnormal value removal and then perform winsorization. FIGS. 5A to 6C show a process for performing threshold value removal and winsorization. For example, assume that the cycle set obtainer 142 obtains the first cycle set shown in FIG. 4C. The length of base cycle C1 is 30 days. The lengths of the reference cycle C2, C3, C4, C5, C6, and C7 are respectively 35, 24, 34, 29, 29, and 29. FIG. 5A is a graph showing an example of the frequency distribution of reference cycles obtained by the modified reference cycle obtainer 143 and also showing an example of the positional relationship between the frequency distribution and the threshold value OF. It should be noted that FIG. 5A shows an example of the frequency distribution of reference cycles for the purpose of illustration and that the frequency distribution does not necessarily coincide with the actual frequency distribution of the reference cycles C2 to C7. FIG. 5B is a diagram showing, as an example, the reference cycles from among which an abnormal value has been removed. For example, assume that the probability of occurrence of a reference cycle having 35 days is less than OF % and that the probability of occurrence of a reference cycle having 24 days, the probability of occurrence of a reference cycle having 29 days, and the probability of occurrence of a reference cycle having 34 days are each greater than or equal to OF %. In this case, the modified reference cycle obtainer 143 removes the reference cycle C2, having 35 days, as an abnormal value from among the reference cycles C2 to C7. Thus, the modified reference cycle obtainer 143 obtains the modified reference cycles C3 to C7, as shown in FIG. 5B. FIG. 5C is a graph showing an example of the frequency distribution of the reference cycles left after removal of the abnormal value. FIG. 5C shows that the reference cycle whose probability of occurrence is less than OF % has been removed.

FIG. 6A is a graph showing an example of the frequency distribution of the reference cycles left after removal of the abnormal value and also showing an example of the positional relationship between the frequency distribution and the threshold value WN. The modified reference cycle obtainer 143 determines the OF-th percentile for abnormal value removal to be the 0th percentile for winsorization. The modified reference cycle obtainer 143 also determines the (100−OF)-th percentile for abnormal value removal to be the 100th percentile for winsorization. The modified reference cycle obtainer 143 then determines the WN-th percentile and the (100−WN)-th percentile within the determined range. FIG. 6B is a diagram showing, as an example, the reference cycles to which winsorization has been applied. For example, assume that the WN-th percentile corresponds to 25 days and that the (100−WN)-th percentile corresponds to 32 days. In this case, as shown in FIG. 6B, the modified reference cycle obtainer 143 changes the length, 24 days, of the reference cycle C3 to 25 days and changes the length, 34 days, of the reference cycle C4 to 32 days. FIG. 6C is a graph showing an example of the frequency distribution of the winsorized reference cycles. In FIG. 6C, a reference cycle having a length below the WN-th percentile has been changed to be at the WN-th percentile, and a reference cycle having a length above the (100−WN)-th percentile has been changed to be at the (100−WN)-th percentile.

The representative value obtainer 144 calculates, for each candidate threshold value obtained by the candidate parameter obtainer 141, a representative value of the modified reference cycles obtained by the modified reference cycle obtainer 143. When the candidate parameter obtainer 141 obtains candidate combinations each including at least a threshold value for abnormal value removal and a threshold value for winsorization, the modified reference cycle obtainer 143 calculates, for each candidate combination, a representative value of the modified reference cycles. If a representative value type used for prediction is predetermined, the representative value obtainer 144 obtains only the predetermined one of the following values: the average value or the median value of the modified reference cycles. On the other hand, if a representative value type used for prediction is not predetermined, the representative value obtainer 144 obtains both the average value and the median value of the modified reference cycles. Specifically, if a representative value type included in the obtained candidate combination is "average value", the representative value obtainer 144 calculates the average value. If the representative value type is "median value", the representative value obtainer 144 calculates the median value. FIG. 7A is a graph showing an example of the frequency distribution of the winsorized reference cycles and also showing an example of the positional relationship between the frequency distribution and a representative value. FIG. 7B is a diagram illustrating an example of how the representative value is determined and how the difference between the representative value and the length of a base cycle is determined. For example, if the representative value type is "average value", the representative value obtainer 144 calculates the average value of the reference cycles shown in FIG. 6C to be 28.8, as shown in FIG. 7B. On the other hand, if the representative value type is "median value", the representative value obtainer 144 determines the median value to be 29. The obtained representative value corresponds to a provisionally predicted menstrual cycle.

The parameter determiner 145 compares, for each candidate threshold value obtained by the candidate parameter obtainer 141 or for each candidate combination, the representative value obtained by the representative value obtainer 144 with the length of the base cycle. The parameter determiner 145 then determines a parameter or a combination used for prediction, based on the result of this comparison. For example, the parameter determiner 145 may calculate the difference between the representative value and the base cycle. For example, as shown in FIG. 7B, the parameter determiner 145 calculates the difference between the length of the base cycle C1, 30, and the average value, 28.8, to be 1.2. The parameter determiner 145 may determine a parameter or a combination that minimizes the calculated difference to be a parameter or a combination used for prediction. The difference between the representative value and the length of the base cycle is the difference between the provisionally predicted menstrual cycle and an actual menstrual cycle. Thus, the smaller this difference is, the higher the accuracy of predicting a menstrual cycle will be.

When the cycle set obtainer 142 obtains a plurality of cycle sets, the modified reference cycle obtainer 143, the representative value obtainer 144, and the parameter determiner 145 process, for each candidate threshold value obtained by the candidate parameter obtainer 141 or each candidate combination, each of the cycle sets. That is, the modified reference cycle obtainer 143 modifies, for each candidate threshold value or for each candidate combination, a plurality of reference cycles in each of the cycle sets, and obtains the modified reference cycles. The representative value obtainer 144 obtains, for each candidate threshold value or for each candidate combination, a representative value of the reference cycles modified in each of the cycle sets. The parameter determiner 145 compares, for each candidate threshold value or for each candidate combination, the representative value obtained for each of the cycle sets with the length of a base cycle in the cycle set.

The parameter determiner 145 may calculate, for example for each candidate parameter or for each candidate combination, the total of differences calculated for the corresponding cycle sets. The parameter determiner 145 may then determine a candidate parameter or a candidate combination whose total of differences is smallest to be a parameter or a combination used for prediction. Hereinafter, the term "candidate" refers to a candidate parameter or a candidate combination. Instead of calculating the total, the parameter determiner 145 may calculate, for example, the average value or the median value.

When determining parameters using the difference between the representative value of each of the cycle sets and the corresponding base cycle, the parameter determiner 145 may or may not weight the difference between the representative value and the base cycle, based on the temporal position of the base cycle included in the cycle set. For example, the older temporal position the base cycle has, the less weight the parameter determiner 145 may assign. The parameter determiner 145 determines parameters to predict the length of the current menstrual cycle. A base cycle with an older temporal position is temporally farther from the current menstrual cycle. Thus, the older temporal position a base cycle has, the lower similarity the base cycle and the current menstrual cycle are likely to have. For this reason, use of parameters determined so that the older temporal position the base cycle has, the less weight is assigned can improve the accuracy of predicting the length of a menstrual cycle.

Figures 8A, 8B:
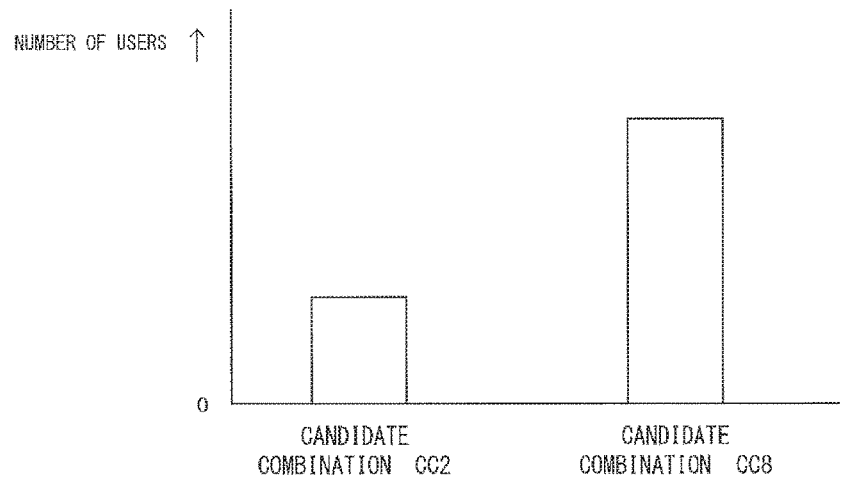
FIG. 8A is a diagram showing an example of calculating the total of differences each of which is the difference between a representative value and a base cycle.
FIG. 8B is a graph showing, as an example, the number of users for whom a first candidate has been determined and the number of users for whom a second candidate has been determined.

FIG. 8A is a diagram showing an example of calculating the total of differences each of which is the difference between a representative value and a length of a base cycle. For example, assume that the candidate combinations shown in FIG. 4A are obtained and that the first to third cycle sets shown in FIG. 4C are obtained. In this case, the parameter determiner 145 calculates, for each candidate combination, a weighted difference between a representative value and a base cycle. For example, the parameter determiner 145 may multiply the difference between the representative value and the base cycle of the first cycle set by a weighting factor of 1, multiply the difference between the representative value and the base cycle of the second cycle set by a weighting factor of 0.8, and multiply the difference between the representative value and the base cycle of the third cycle set by a weighting factor of 0.5. The weighting factor of each cycle set may be freely set, on condition that less weight is assigned to a base cycle with an older temporal position.

Differences comparable to a difference obtained using a candidate that minimizes the difference between a representative value and a base cycle may be calculated for one or more other candidates. That is, there may be a plurality of candidates that enable provisional predictions with comparably high accuracy. A candidate that minimizes the difference between a representative value and a base cycle is referred to as a first candidate. A candidate for which a difference within a predetermined range from the difference obtained for the first candidate is obtained is referred to as a second candidate. Also in this case, the parameter determiner 145 may determine the first candidate to be a parameter or a combination used for prediction. Alternatively, the parameter determiner 145 may determine the first candidate or the second candidate to be a parameter or a combination used for prediction, based on a predetermined criterion. There may be a plurality of candidates each for which a difference within a predetermined range from the difference obtained for the first candidate is obtained. In that case, the parameter determiner 145 may identify only less than a predetermined number of these candidates as second candidates or may identify all the candidates as second candidates.

For example, the parameter determiner 145 may obtain the number of users for whom the first candidate has been determined as a parameter or a combination used for prediction and the number of users for whom a second candidate has been determined as a parameter or a combination used for prediction, among users different from the target woman whose menstrual date is to be predicted. The parameter determiner 145 can obtain these numbers of users, based on the parameter information stored in the parameter DB 12*d*. For example, the parameter determiner 145 may determine a candidate that has been most commonly obtained for users, among the first candidate and the one or more second candidates, to be a parameter or a combination used for prediction. The reason is that a parameter used for many users is likely to be a parameter that can be used to make predictions for various users.

FIG. 8B is a graph showing, as an example, the number of users for whom the first candidate has been determined and the number of users for whom a second candidate has been determined. Assume that a candidate combination CC2 is identified as the first candidate and that a candidate combination CC8 is identified as the second candidate. As shown in FIG. 8B, the number of users for whom the candidate combination CC8 has been determined exceeds the number of users for whom the candidate combination CC2 has been determined. Thus, the parameter determiner 145 may determine the candidate combination CC8 to be a parameter combination used for prediction.

There is a case where a plurality of pieces of parameter information are stored for one user. In this case, the parameter determiner 145 may count the number of users, for example, using parameter information including the latest registration date. Alternatively, the parameter determiner 145 may count how often the first candidate and the second candidate(s) each have been determined to be a parameter or a combination used for prediction, based on the plurality of pieces of parameter information. The parameter determiner 145 may then determine, for example, that the most frequent candidate, among the first candidate and the second candidate(s), has been determined to be a parameter or a combination used for prediction.

The parameter determiner 145 may obtain the number of users for whom the first candidate has been determined and who have the same type of characteristics as the target woman. The parameter determiner 145 may obtain the number of users for whom a second candidate has been determined and who have the same type of characteristics as the target woman. The parameter determiner 145 may then determine a parameter or a combination used for prediction, based on the obtained numbers of users. The reason is that the menstruation or the menstrual cycle of a user who has the same characteristics as target woman is likely to show a tendency similar to the menstruation or the menstrual cycle of the target woman. Examples of the characteristics include ages, age groups, the seasons or the months when parameters or combinations used for prediction were determined, body temperature change tendencies, the lengths of low-temperature phases, and the lengths of high-temperature phases. The parameter determiner 145 can obtain ages or age groups, for example, based on the member information DB 12*a*. The parameter determiner 145 can also obtain the seasons or the months when parameters or combinations used for prediction were determined, for example, based on the parameter information stored in the parameter DB 12*d*.

The parameter determiner 145 can also obtain body temperature change tendencies, the lengths of low-temperature phases, and the lengths of high-temperature phases, based on the body temperature DB 12b and the menstrual date DB 12c. For example, the same type of characteristics as the target woman may be the same characteristics as the target woman, characteristics within a predetermined range from the characteristics of the target woman, or characteristics similar to the characteristics of the target woman.

3-1-2. Prediction of Menstrual Date

The cycle-based predictor 146 predicts the target woman's current menstrual cycle using the parameter or the combination determined by the parameter determiner 145. Specifically, the cycle-based predictor 146 obtains a plurality of past menstrual cycles of the target woman whose menstrual date is to be predicted. The cycle-based predictor 146 then applies predetermined processing to an outlier identified based on the threshold value determined to be a parameter, among the obtained menstrual cycles, to obtain a plurality of modified menstrual cycles. More particularly, the cycle-based predictor 146 removes an abnormal value from the menstrual cycles or winsorizes the menstrual cycles. Alternatively, the cycle-based predictor 146 performs abnormal value removal and then further performs winsorization. When the parameter determiner 145 determines a threshold value for abnormal value removal, the cycle-based predictor 146 removes an abnormal value using this threshold value. When the parameter determiner 145 determines a threshold value for winsorization, the cycle-based predictor 146 performs winsorization using this threshold value. The cycle-based predictor 146 obtains a representative value of the modified menstrual cycles as a predicted length of the current menstrual cycle. When the parameter determiner 145 determined "average" to be a representative value type, the cycle-based predictor 146 calculates the average value of the modified menstrual cycles. When the parameter determiner 145 determined "median value" to be a representative value type, the median value of the modified menstrual cycles is calculated. Subsequently, the obtained representative value is added to the first day of the current menstrual cycle, to calculate a predicted menstrual date.

There may be a case where the frequency distribution of the past menstrual cycles has two local maximum values. In this case, for example, the cycle-based predictor 146 may determine only one representative value for the whole frequency distribution. Alternatively, for example, the cycle-based predictor 146 may divide the distribution of the menstrual cycles into sub-distributions at the position of a local minimum frequency of cycle. For example, the cycle-based predictor 146 may obtain a representative value for each sub-distribution. The cycle-based predictor 146 may add, for each representative value, the representative value to the first day of the current menstrual cycle, to calculate a predicted menstrual date. That is, the cycle-based predictor 146 may predict two next menstrual dates. In this case, the cycle-based predictor 146 may cause the user terminal 2 to display, for example, "A predicted next menstrual date for a short cycle is X, and a predicted next menstrual date for a long cycle is Y." Among the two predicted menstrual dates, X is nearer to today while Y is farther from today. When there are three or more local maximum values, for example, the cycle-based predictor 146 may predict only one next menstrual date without dividing the distribution of the menstrual cycles.

All parameters used in the cycle-based prediction method may be predetermined. For example, the parameters may be stored in the storage unit 12. In this case, a candidate parameter obtainer 141, the cycle set obtainer 142, the modified reference cycle obtainer 143, the representative value obtainer 144, and the parameter determiner 145 are unnecessary.

3-2. Temperature-Based Prediction Method

Figure 9:
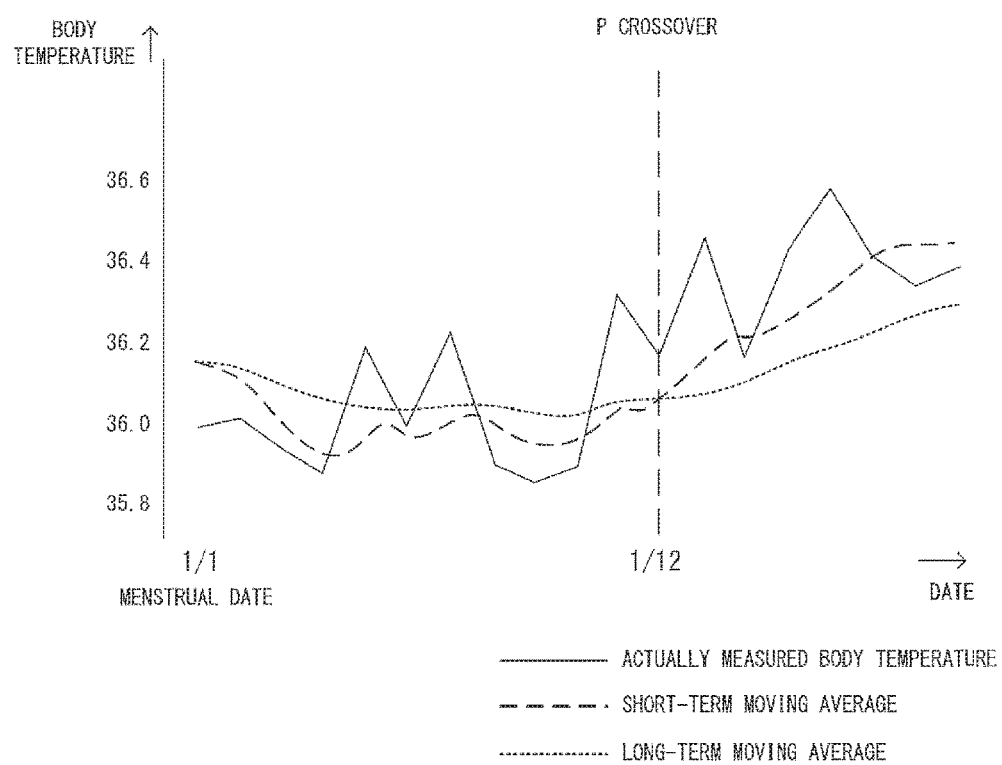
FIG. 9 is a diagram showing, as an example, a graph of body temperatures actually measured during the current menstrual cycle, a short-term moving average line of the body temperatures, and a long-term moving average line of the body temperatures.

When using the temperature-based prediction method, the system controller 14 calculates, for example for each day, short-term and long-term moving averages of actually measured body temperatures of a target woman whose menstrual date is to be predicted. The system controller 14 then identifies the timing at which the short-term moving average exceeds the long-term moving average during the current menstrual cycle. A timing at which a short-term moving average exceeds a corresponding long-term moving average is, for example, a timing that is among the timings at which the short-term and long-term moving average lines cross and immediately after which the short-term moving average is higher than the long-term moving average. Such a crossing of moving average lines is referred to as a P crossover (positive crossover). When the short-term moving average exceeds the long-term moving average, the P crossover occurs. FIG. 9 is a diagram showing, as an example, a graph of body temperatures actually measured during the current menstrual cycle, a short-term moving average line of the body temperatures, and a long-term moving average line of the body temperatures. As shown in FIG. 9, the current menstrual cycle started on January 1, and the P crossover occurred on January 12. The system controller 14 predicts the next menstrual date or estimates the arrival of an ovulation date, based on the identified timing. Alternatively, the system controller 14 may predict the next menstrual date and also estimate the arrival of an ovulation date.

As described above, a menstrual cycle typically includes a low-temperature phase and a high-temperature phase. On an ovulation date in a menstrual cycle, an ovum is discharged from an ovarian follicle. After that, the ovarian follicle is turned into a corpus *luteum*. This corpus *luteum* secretes corpus *luteum* hormones. The corpus *luteum* hormones cause an elevation in body temperature and the transition from the low-temperature phase to the high-temperature phase. Once the corpus *luteum* regresses, the secretion of corpus *luteum* hormones ends. Then, an endometrium cannot be maintained, and menstruation begins. After the secretion of corpus *luteum* hormones ends, the body temperature falls. The low-temperature phase of the next menstrual cycle thus begins. Corpus *luteum* hormones have very stable life span. For example, corpus *luteum* hormones typically have a life span of 14±2 days.

The transition date at which the transition from the low-temperature phase to the high-temperature phase occurs or a date close to the transition date is likely to be an ovulation date. However, changes in actual body temperature are sometimes unstable. For example, the body temperature may fluctuate widely before and after the timing at which the transition from the low-temperature phase to the high-temperature phase should occur. Thus, it is difficult to determine whether the high-temperature phase has begun, based on only body temperatures actually measured on a daily basis.

In contrast to this, the temperature-based prediction method in this embodiment uses moving averages to smooth time-series body temperature. A short-term moving average indicates the tendency of body temperature during the latest short period. A long-term moving average indicates the tendency of body temperature for a long period. Thus, based on a timing at which the short-term moving average exceeds the long-term moving average, the timing of the transition from the low-temperature phase to the high-temperature phase can be correctly identified. Accordingly, the arrival of an ovulation date can be estimated accurately. In the example of FIG. 9, an ovulation date is likely to have come on or around January 12.

Even for the same target woman, the length of her low-temperature phase is relatively variable from menstrual cycle to menstrual cycle. On the other hand, the length of a high-temperature phase is relatively stable. The reason is that the length of a high-temperature phase corresponds to the life span of a corpus *luteum*. Thus, if the date on which an ovulation date came can be estimated, the next menstrual cycle can be predicted.

A calculated moving average may be any type of moving average. For example, a simple moving average, a weighted moving average, or an exponential moving average may be calculated. Any known formula can be used as a formula for calculating an exponential moving average. For example, assume that p is the length of a period. The length p is actually a short term length or a long term length. In this case, an exponential moving average EMAp(t) t days after the start date of calculation may be calculated, for example, using the following Equation 1:

[Math. 1]

$$EMA_p(t) = \begin{cases} e(0)(t=0) \\ d \cdot EMA_p(t-1) + (1-d) \cdot e(t)(t>0) \end{cases} \quad \text{Equation 1}$$

e(t) is a body temperature actually measured t days after. d is a smoothing factor. d may be calculated using the following Equation 2:

[Math. 2]

$$d = \exp\left(\frac{-\ln(2)}{p}\right) \quad \text{Equation 2}$$

3-2-1. Determination of Parameters

The period length determiner 147 determines parameters used in the temperature-based prediction method in order to estimate the arrival of an ovulation date or to predict a menstrual date using the temperature-based prediction method. The determined parameters are a short term length and a long term length that are used to calculate a moving average.

For example, for a simple moving average or a weighted moving average, the short term length and the long term length each indicate the number of actually measured body temperatures that are bases for calculating the average value. Let s denote the short term length and let l denote the long term length. The short-term moving average is an average value of body temperatures actually measured for the last s days. The long-term moving average is an average value of body temperatures actually measured for the last l days. For an exponential moving average, the short term length and the long term length are each one of the parameters for calculating the average. Each time the exponential moving average is calculated, a weight for actually measured body temperatures, which is used for the calculation, decreases exponentially. Thus, the short term length and the long term length may be each, for example, the number of days required for the weight for actually measured body temperatures to become less than or equal to a predetermined value. In Equations 1 and 2, the short term length and the long term length are each the number of days required for the weight for actually measured body temperatures to become less than or equal to one half.

Figure 10:
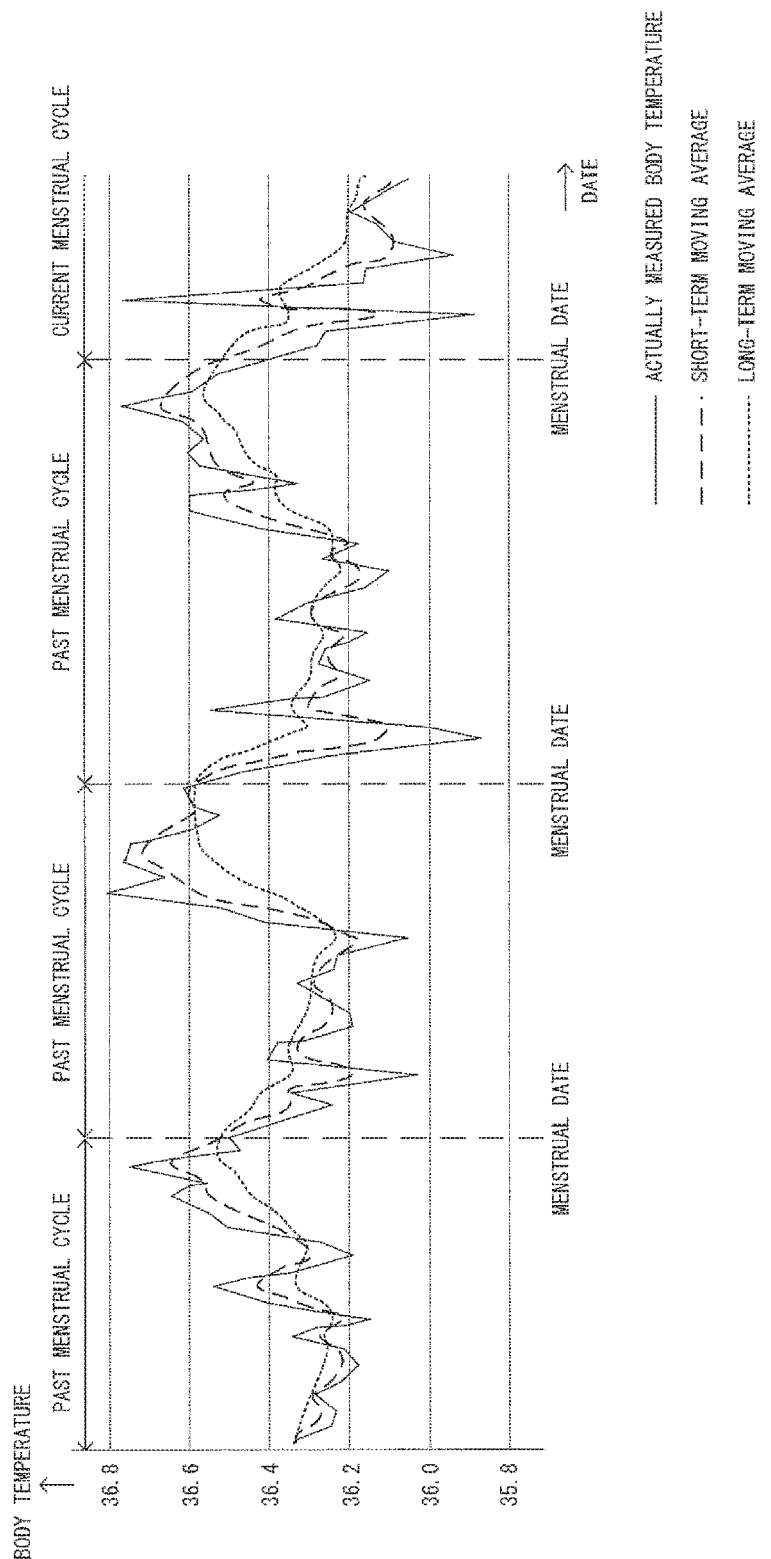
FIG. 10 is a diagram showing, as an example, a graph of body temperatures during the past three menstrual cycles, a short-term moving average line of the body temperatures, and a long-term moving average line of the body temperatures.

For example, the period length determiner 147 may determine parameters used in the temperature-based prediction method, using target woman's body temperatures actually measured during the past one or more menstrual cycles. The past one or more menstrual cycles may be, for example, menstrual cycles continuous with the current menstrual cycle. When past two or more menstrual cycles are used, for example, these menstrual cycles may be continuous. The period length determiner 147 may calculate a short-term moving average and a long-term moving average across the past one or more menstrual cycles, for example, using a candidate short term length and a candidate long term length that are used as parameters. FIG. 10 is a diagram showing, as an example, a graph of body temperatures during the past three menstrual cycles, a short-term moving average line of the body temperatures, and a long-term moving average line of the body temperatures.

The period length determiner 147 determines a short term length and a long term length that are used as parameters so that the timing(s) at which a short-term moving average of body temperatures measured during the past one or more menstrual cycles falls below a corresponding long-term moving average coincides with menstrual date(s) that are the first day(s) of the past one or more menstrual cycles. A timing at which a short-term moving average falls below a corresponding long-term moving average is, for example, a timing that is among the timings at which the short-term and long-term moving average lines cross and immediately after which the short-term moving average is lower than the long-term moving average. Such a crossing of moving average lines is referred to as an N crossover (negative crossover). When the short-term moving average falls below the long-term moving average, the N crossover occurs. FIG. 11 is a diagram showing an example of the relationship between the short-term moving average line of the body temperatures and the long-term moving average line of the body temperatures during the past three menstrual cycles. In the example of FIG. 11, each of the three menstrual dates almost coincides with the timing of an N crossover.

As described above, the date on which the transition from a high-temperature phase to the low-temperature phase of the next menstrual cycle is likely to be an actual menstrual date. For this reason, the period length determiner 147 determines the short term length and the long term length so that the timing of an N crossover coincides with an actual menstrual date, thus improving the accuracy of estimating an ovulation date using moving averages or the accuracy of predicting a menstrual date.

Specifically, the period length determiner 147 may determine the short term length and the long term length, for example, so as to minimize a function err that indicates the difference between the menstrual date and the timing of the N crossover. The parameters of the function err are the short term length s and the long term length l. For convenience, let x denote the transpose of a matrix (s, l) and let the matrix x be the parameters of err. In this case, for example, err may be expressed as the following Equation 3:

[Math. 3]

$$err(x) = \frac{1}{n}\sum_{i}^{n} |menday(i) - ncoday(x, i)| \quad \text{Equation 3}$$

menday(i) is the first day of the i-th of a past n menstrual cycles, that is, a menstrual date. ncoday(x, i) is a date nearest to menday(i) among the occurrence dates of N crossovers identified based on short-term and long-term moving averages calculated using x. The period length determiner 147 may solve, for example, a convex optimization problem to find x that minimizes err(x). This problem may be expressed by the following Equation 4:

$$\min\{err(x){:}x{=}(s,l)^T, s{\in}X, l{\in}Y, s{<}l\} \quad \text{[Math. 4] Equation 4}$$

x and y are each a group of freely-selected natural numbers. The period length determiner 147 may use any algorithm that can solve this optimization problem. For example, the period length determiner 147 may use a simplex algorithm. Alternatively, when an upper limit is preset on a long term length, the period length determiner 147 may calculate err for every pair of short and long term lengths, and then determine a pair of short and term lengths corresponding to the smallest calculated err to be a short term length and a long term length that are used to estimate the arrival of an ovulation date or to predict the next menstrual date.

The period length determiner 147 may determine the short term length and the long term length so that the difference between a menstrual date and the timing at which a short-term moving average of body temperatures during the past one or more menstrual cycles falls below a corresponding long-term moving average is small, and also so that, for example, the value of integral of the difference between the short-term moving average and the long-term moving average across the past one or more menstrual cycles is large. That is, for example, in FIG. 11, the period length determiner 147 may determine the short term length and the long-term length so that the area of the region enclosed by the short-term moving average line and the long-term moving average line is as small as possible. The reason is to identify N crossovers. If the overall difference between the short-term moving average and the long-term moving average is small, it may be difficult to identify N crossovers or there may be cases where a plurality of N crossovers occur within one menstrual cycle. The definite integral of the difference between the short-term moving average and the long-term moving average is expressed by the following Equation 5:

$$area(x){=}\int_0^{TE} |EMA_s(t){-}EMA_l(t)| dx \quad \text{[Math. 5] Equation 5}$$

TE is the number of days between the first day of the first menstrual cycle and the last day of the last menstrual cycle inclusive, among the past one or more menstrual cycles. EMAs is a short-term moving average, where s is a short term length. EMAl is a long-term moving average, where l is a long term length.

In order to satisfy the above two requirements, for example, a function f(x) may be used. The function f(x) decreases as the difference between a menstrual date and the timing at which the short-term moving average falls below the long-term moving average increases. In addition, the function f(x) increases as the definite integral of the difference between the short-term moving average and the long-term moving average increases. For example, f(x) may be expressed as the following Equation 6:

[Math. 6]

$$f(x) = \alpha \frac{1}{1 - err(x)} + \beta \cdot area(x) \quad \text{Equation 6}$$

α and β are constants. Equation 6 is an example of the equation of the function f(x). The function f(x) may be calculated using an equation different from Equation 6.

The period length determiner 147 may determine the short term length and the long term length, for example, so as to maximize f. For example, the period length determiner 147 may solve a convex optimization problem to find x that maximizes f. This problem may be expressed by the following Equation 7:

$$\max\{f(x){:}x{=}(s,l)^T, s{\in}X, l{\in}Y, s{<}l\} \quad \text{[Math. 7] Equation 7}$$

The period length determiner 147 may use any algorithm that can solve this optimization problem. For example, the period length determiner 147 may use a simplex algorithm. Alternatively, when an upper limit is preset on a long term length, the period length determiner 147 may calculate f for every pair of short and long term lengths, and then determine a pair of short and term lengths corresponding to the largest calculated f to be a short term length and a long term length that are used to estimate the arrival of an ovulation date or to predict the next menstrual date.

The period length determiner 147 may determine the short term length and the long term length so as to minimize function g(x). The function g(x) increases as the difference between a menstrual date and the timing at which the short-term moving average falls below the long-term moving average increases. In addition, the function g(x) decreases as the definite integral of the difference between the short-term moving average and the long-term moving average increases. Reversing the sign of the function f(x) changes the above problem to an optimization problem of finding the short term length and the long term length that minimize -f(x). Thus, the problem of optimizing the function f(x) and the problem of optimizing the function g(x) are substantially the same.

3-2-2. Estimation of Ovulation Date and Prediction of Menstrual Date

The timing identification unit 148 calculates a short-term moving average and a long-term moving average across the current menstrual cycle, using the short term length and the long term length that are determined by the period length determiner 147. When calculating exponential moving averages, for example, the timing identification unit 148 may start the calculation from any date during the past one or more menstrual cycles. The timing identification unit 148 then identifies the timing at which the short-term moving average exceeds the long-term moving average, that is, the occurrence date of a P crossover, during the current menstrual cycle.

The temperature-based predictor 149 estimates the arrival of an ovulation date or predicts the next menstrual date, based on the timing identified by the timing identification unit 148.

When estimating the arrival of an ovulation date, the temperature-based predictor 149 may estimate the occurrence date of the P crossover to be the ovulation date. Alternatively, the temperature-based predictor 149 may estimate a predetermined days before or predetermined days after the P crossover occurred to be the ovulation date. Alternatively, if an ovulation test identifies the target woman's ovulation date during a past menstrual cycle, the temperature-based predictor 149 may calculate the difference between the identified ovulation date and the date on which a P crossover occurred during the past menstrual cycle. The temperature-based predictor 149 may then add the calculated difference to the date on which the P crossover occurred during the current menstrual cycle to calculate an estimated ovulation date.

Figure 12A:
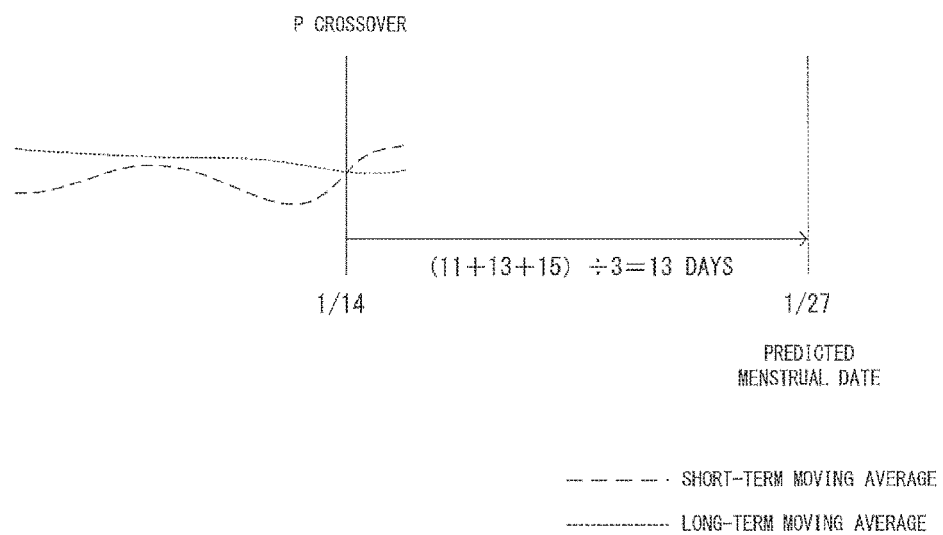
FIG. 12A is a diagram illustrating an example of how a predicted menstrual date is calculated.

When predicting the next menstrual date, for example, the temperature-based predictor 149 may add a predetermined number of days to the occurrence date of the P crossover to calculate a predicted menstrual date or may add a predetermined number of days to the estimated ovulation date to calculate a predicted menstrual date. The number of added days may be predetermined, for example, to be within a range of 14±2 days. Alternatively, the temperature-based predictor 149 may calculate a representative value of the numbers of days each between the date on which a P crossover occurred and the date on which a subsequent N crossover occurred during the past one or more menstrual cycles, for example, based on the short-term moving average and the long-term moving average across the past one or more menstrual cycles. The temperature-based predictor 149 may calculate the average value or the median value of the numbers of days. The temperature-based predictor 149 may then add the calculated representative value, for example, to the date on which a P crossover occurred during the current menstrual cycle to calculate a predicted menstrual date. FIG. 12A is a diagram illustrating an example of how a predicted menstrual date is calculated. For example, in the example of FIG. 11, the numbers of days each between the date on which a P crossover occurred and the date on which a subsequent N crossover occurred during one of the three menstrual cycles are 11, 13, and 15. Thus, the average is 13. As shown in FIG. 12A, during the current menstrual cycle, a P crossover occurred on July 14. Thus, the temperature-based predictor 149 predicts the next menstrual date to be July 27.

It is noted that an ovulation date during the current menstrual cycle may be estimated or an ovulation date during a past menstrual cycle may be estimated. For example, the timing identification unit 148 may calculate a short-term moving average and a long-term moving average across a certain past menstrual cycle, using the short term length and the long term length that are determined by the period length determiner 147, to identify the timing at which the short-term moving average exceeds the long-term moving average during the menstrual cycle. The temperature-based predictor 149 may then estimate an ovulation date during the menstrual cycle, based on the identified timing. A short term length and a long term length that are used in the temperature-based prediction method may be predetermined. For example, a short term length and a longterm length may be prestored in the storage unit 12. In this case, the period length determiner 147 is unnecessary.

3-3. Switch of Prediction Method

According to the cycle-based prediction method, whether the current phase is a low-temperature phase or during a high-temperature phase, the next menstrual cycle can be predicted if the length of each of the past three or more menstrual cycles has been identified. On the other hand, according to the temperature-based prediction method, the next menstrual date can be accurately predicted based on the timing at which a short-term moving average of body temperatures exceeds a corresponding long-term moving average, that is, the timing at which a P crossover occurred. However, the temperature-based prediction method cannot be used if no P crossover has occurred yet during the current menstrual cycle.

Thus, if the timing identification unit 148 has not identified the timing at which a short-term moving average of body temperatures exceeds a corresponding long-term moving average during the current menstrual cycle, the cycle-based predictor 146 may predict the next menstrual date. On the other hand, if the timing identification unit 148 has identified the timing at which the short-term moving average exceeds the long-term moving average, the temperature-based predictor 149 may predict the next menstrual date.

Figure 12B:
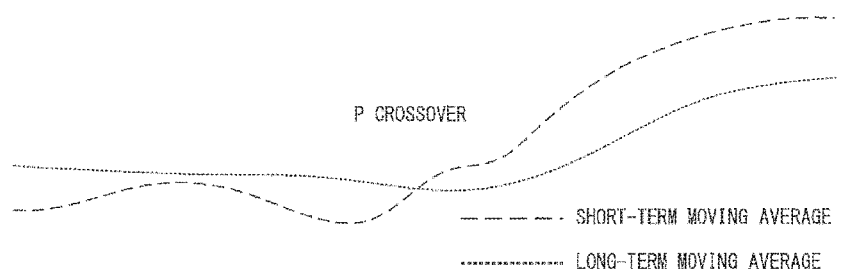
FIG. 12B is a diagram showing an example of determining which method to use to predict the next menstrual date.

FIG. 12B is a diagram showing an example of determining which method to use to predict the next menstrual date. As shown in FIG. 12B, the short-term moving average are lower than the long-term moving average from January 13 to 16. Thus, during this period, the cycle-based predictor 146 predicts the next menstrual date using the cycle-based prediction method. On January 17, a P crossover occurs. Thus, on and after January 17, the temperature-based predictor 149 predicts the next menstrual date using the temperature-based prediction method.

For example, the cycle-based predictor 146 may always predicts the next menstrual date in any situation. In this case, the temperature-based predictor 149 is unnecessary. Also for example, if the timing at which a P crossover occurred during the current menstrual cycle has not yet been identified, the system controller 14 may predict the next menstrual date using a method other than the cycle-based prediction method described in Section 3-1. For example, the system controller 14 may use any method that predicts the next menstrual date by adding a representative value of the lengths of the past one or more cycles to a menstrual date that is the first day of the current menstrual cycle. In this case, for example, at least one of the past one or more cycle may be modified or changed in length. After the timing at which a P crossover occurred has been identified, the temperature-based predictor 149 may predict the next menstrual date. Alternatively, for example, if the timing at which a P crossover occurred during the current menstrual cycle has not yet been identified, the system controller 14 may not predict the next menstrual date. After the timing at which a P crossover occurred has been identified, the temperature-based predictor 149 may predict the next menstrual date. In this case, the cycle-based predictor 146 is unnecessary.

4. How Information Processing System Works

The following describes how the information processing system S works, with reference to FIGS. 13 to 19.

Figure 13:
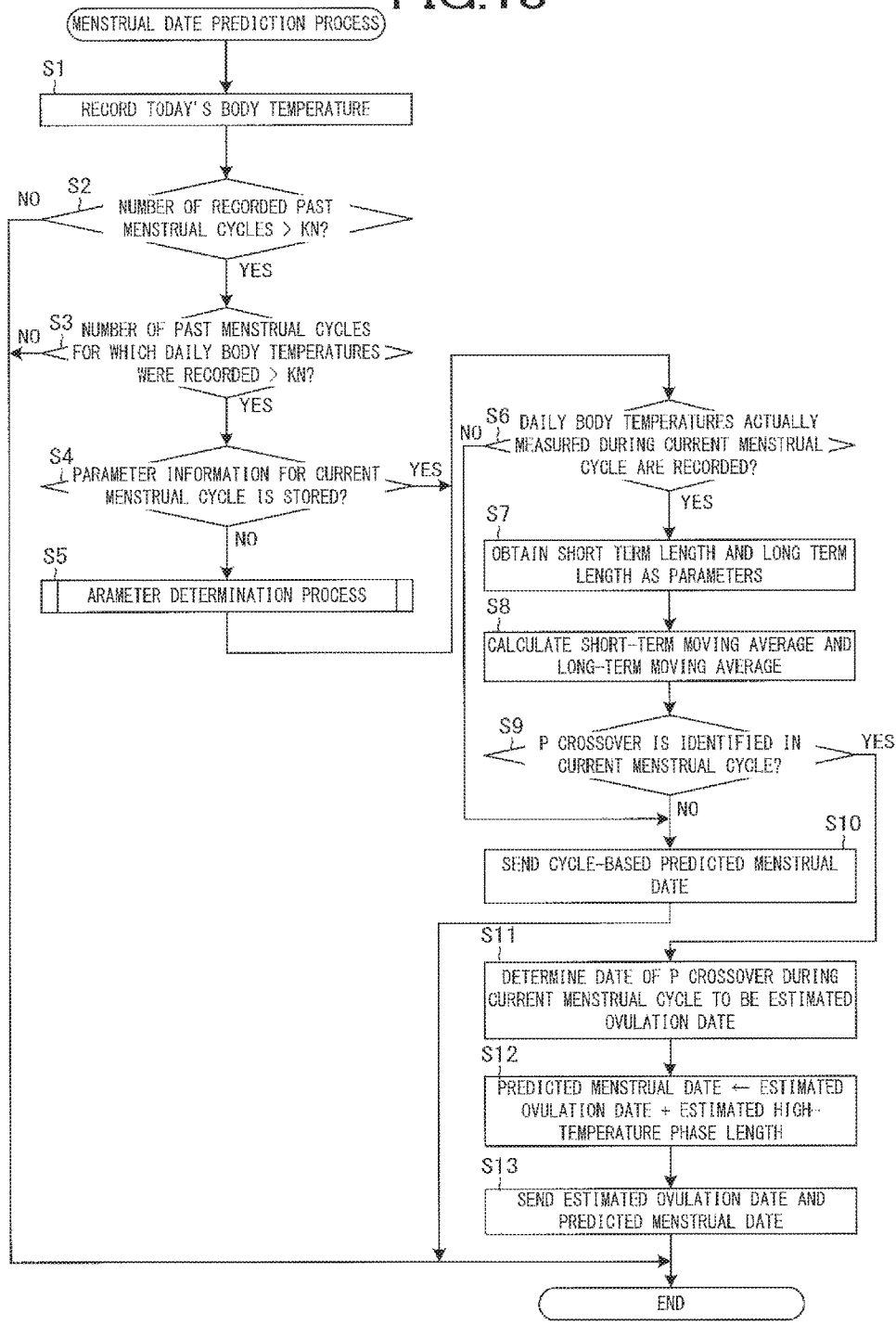
FIG. 13 is a flowchart showing an example of a menstrual date prediction process in the system controller 14 of the information processing server 1 according to an embodiment.

FIG. 13 is a flowchart showing an example of a menstrual date prediction process in the system controller 14 of the information processing server 1 according to this embodiment. For example, a user operates her user terminal 2 to run a terminal application program. The user then takes her today's body temperature with her thermometer 3. Subsequently, the user terminal 2 receives the measured body temperature as an actual measurement from the thermometer 3. The user terminal 2 sends the actually measured body temperature and the user ID of the user, who uses the user terminal 2, to the information processing server 1. When the actually measured body temperature and the user ID are received from the user terminal 2, the system controller 14 performs the menstrual date prediction process. In this case, the user identified by the user ID is a target woman whose next menstrual date is to be predicted.

As shown in FIG. 13, the temperature-based predictor 149 records the received actual measurement (Step S1). Specifically, the temperature-based predictor 149 obtains today's date as a measurement date. The temperature-based predictor 149 then stores the received actual measurement and the received user ID in the body temperature DB 12b.

Subsequently, the cycle-based predictor 146 determines whether the number of past menstrual cycles recorded for the user identified by the target woman's user ID is greater than a prestored threshold value KN (Step S2). For example, the cycle-based predictor 146 searches the menstrual date DB 12c for menstrual dates corresponding to the target woman's user ID. The cycle-based predictor 146 subtracts 1 from the number of menstrual dates found by this search to calculate the number of the past menstrual cycles. The threshold value KN may indicate, for example, any number greater than or equal to two. If the cycle-based predictor 146 determines that the number of the past menstrual cycles is greater than the threshold value KN (YES in Step S2), the menstrual date prediction process proceeds to S3. On the other hand, if it determines that the number of the past menstrual cycles is not greater than the threshold value KN (NO in Step S2), the cycle-based predictor 146 terminates the menstrual date prediction process.

In Step S3, the temperature-based predictor 149 determines whether the number of past menstrual cycles for which actually measured daily body temperatures were recorded is greater than the threshold value KN. For example, the temperature-based predictor 149 sorts the menstrual dates found in Step S2 in ascending order. The temperature-based predictor 149 identifies a menstrual cycle for each pair of two adjacent menstrual dates, among the sorted menstrual dates. One menstrual date starts on a menstrual date and ends on the day before the next menstrual date. The temperature-based predictor 149 searches, for each menstrual cycle, the body temperature DB 12b for body temperatures that correspond to the target woman's user ID and that were actually measured between the first day and the last day of the menstrual cycle inclusive. If the search has found body temperatures actually measured every day between the first day and the last day inclusive, the temperature-based predictor 149 increases by one the number of past menstrual cycles for which actually measured daily body temperatures were recorded. If the temperature-based predictor 149 determines that the number of menstrual cycles thus counted is greater than threshold value KN (YES in Step S3), the menstrual date prediction process proceeds to Step S4. If it determines that the number of past menstrual cycles for which actually measured daily body temperatures were recorded is not greater than the threshold value KN (NO in Step S3), the cycle-based predictor 149 terminates the menstrual date prediction process. If a body temperature actually measured on some day in a certain menstrual cycle is not recorded, the temperature-based predictor 149 may interpolate a body temperature actually measured on the some day, using body temperatures actually measured on the day before and after the some day. In this manner, the temperature-based predictor 149 may increase the number of menstrual cycles for which actually measured daily body temperatures were recorded. Alternatively, for example, the temperature-based predictor 149 may send, to the user terminal 2, a message prompting the user to enter a body temperature measured on a day for which no actually measured body temperature is recorded. The temperature-based predictor 149 may then obtain, as an actual measurement, the body temperature entered by the user from the user terminal 2.

In Step S4, the system controller 14 determines whether parameter information for the current menstrual cycle is stored. For example, the system controller 14 identifies the latest of the menstrual dates found in Step S2 as the first day of the current menstrual cycle. Subsequently, the system controller 14 searches the parameter DB 12d for parameter information corresponding to the target woman's user ID and stored on or after the first day of the current menstrual cycle. If the system controller 14 determines, based on the result of the search, that the parameter information is stored in the parameter DB 12d (YES in Step S4), the menstrual date prediction process proceeds to Step S6. On the other hand, if the system controller 14 determines that the parameter information is not stored in the parameter DB 12d (NO in Step S4), the menstrual date prediction process proceeds to Step S5. In Step S5, the system controller 14 performs a parameter determination process. In the parameter determination process, the system controller 14 generates parameters for the cycle-based prediction method and parameters for the temperature-based prediction method. The system controller 14 also predicts the next menstrual date by the cycle-based prediction method. The system controller 14 also estimates the length of the high-temperature phase of the current menstrual cycle by the temperature-based prediction method. The system controller 14 then generates parameter information for the current menstrual cycle. The parameter determination process will be described in detail later. Next, the system controller 14 causes the menstrual date prediction process to proceed to Step S6.

In Step S6, the temperature-based predictor 149 determines whether daily body temperatures actually measured during the current menstrual cycle are recorded. For example, the temperature-based predictor 149 searches the body temperature DB 12b for body temperatures that correspond to the target woman's user ID and that were actually measured between the first day of the current menstrual cycle and today inclusive. If the search has found body temperatures actually measured every day between the first day and today inclusive, the temperature-based predictor 149 determines that daily body temperatures actually measured during the current menstrual cycle are recorded (YES in Step S6). In this case, the temperature-based predictor 149 causes the menstrual date prediction process to proceed to Step S7. On the other hand, if no body temperature actually measured on at least one day between the first day and today inclusive has not been found, the temperature-based predictor 149 determines that daily body temperatures actually measured during the current menstrual cycle are not recorded (NO in Step S6). In this case, the temperature-based predictor 149 causes the menstrual date prediction process to proceed to Step S10. The temperature-based predictor 149 may determine by interpolation a body temperature for a day for which no actually measured body temperature is recorded or may prompt the user to enter a body temperature measured on a day for which no actually measured body temperature is recorded.

In Step S7, the timing identification unit 148 obtains a short term length and a long term length from the parameter information for the current menstrual cycle. Based on the daily body temperatures actually measured during the current menstrual cycle, the short term length, and the long term length, the timing identification unit 148 then calculates day-to-day short-term and long-term moving averages of body temperatures actually measured between the first day of the current menstrual cycle and today inclusive (Step S8). Subsequently, the timing identification unit 148 determines whether a P crossover is identified in the current menstrual cycle (Step S9). For example, if the short-term moving average on a certain day is lower than the corresponding long-term moving average and the short-term moving average one day after the day is higher than the corresponding long-term moving average, the timing identification unit 148 may determine that a P crossover occurred. In this case, the timing identification unit 148 identifies, for example, one of these two days as the occurrence date of the P crossover. For example, the timing identification unit 148 may identify the day on which the difference between the short-term moving average and the long-term moving average is smaller as the occurrence date of the P crossover. Alternatively, for example, if the short-term moving average on a certain day is lower than the corresponding long-term moving average, the short-term moving average one day after the certain day is equal to the corresponding long-term moving average, and the short-term moving average two days after the certain day is higher than the corresponding long-term moving average, the timing identification unit 148 may determine that a P crossover occurred. In this case, the timing identification unit 148 may identify, for example, the middle of these three days as the occurrence date of the P crossover. If the adding unit 148 determines that a P crossover is identified (YES in Step S9), the menstrual date prediction process proceeds to Step S11. On the other hand, if the adding unit 148 determines that a P crossover is not identified (NO in Step S9), the menstrual date prediction process proceeds to Step S10.

In Step S10, the cycle-based predictor 146 sends a predicted menstrual date included in the parameter information for the current menstrual cycle to the user terminal 2, and then terminates the menstrual date prediction process. The user terminal 2 displays the predicted menstrual date received from the information processing server 1 on its screen.

In Step S11, the temperature-based predictor 149 determines an estimated ovulation date, based on the date on which the P crossover occurred during the current menstrual cycle. For example, the temperature-based predictor 149 may determine the occurrence date of the P crossover to be the estimated ovulation date. Subsequently, the temperature-based predictor 149 adds an estimated high-temperature phase length included in the parameter information for the current menstrual cycle to the occurrence date of the P crossover to calculate a predicted menstrual date (Step S12). After that, the temperature-based predictor 149 sends the estimated ovulation date and the predicted menstrual date to the user terminal 2 (Step S13), and then terminates the menstrual date prediction process. The user terminal 2 displays the estimated ovulation date and the predicted menstrual date that are received from the information processing server 1 on its screen.

Figure 14:
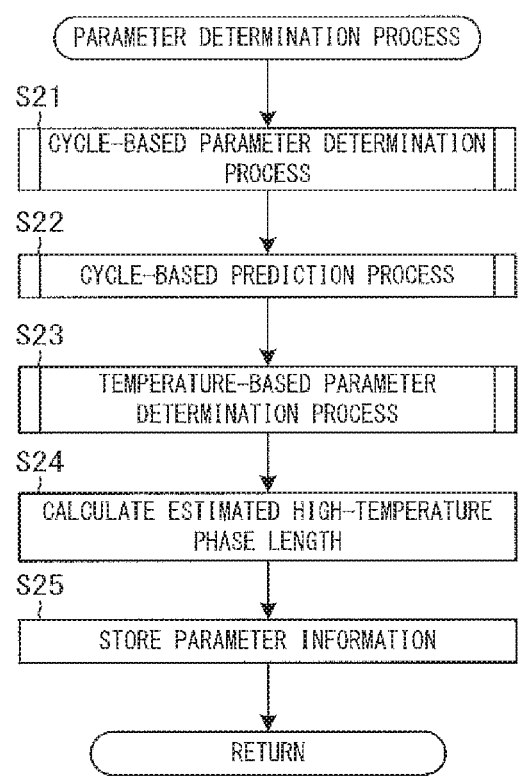
FIG. 14 is a flowchart showing an example of a parameter determination process in the system controller 14 of the information processing server 1 according to an embodiment.

FIG. 14 is a flowchart showing an example of the parameter determination process in the system controller 14 of the information processing server 1 according to this embodiment. As shown in FIG. 14, the system controller 14 performs a cycle-based parameter determination process (Step S21). In the cycle-based parameter determination process, the system controller 14 determines parameters used in the cycle-based prediction method. The cycle-based parameter determination process will be described in detail later. Subsequently, the cycle-based predictor 146 performs a cycle-based prediction process (Step S22). In the cycle-based prediction process, the cycle-based predictor 146 determines a predicted menstrual date by the cycle-based prediction method. The cycle-based prediction process will be described in detail later.

Next, the period length determiner 147 performs a temperature-based parameter determination process (Step S23). In the temperature-based parameter determination process, the period length determiner 147 determines parameters used in the temperature-based prediction method. The temperature-based parameter determination process will be described in detail later. After that, the temperature-based predictor 149 identifies on what date a P crossover occurred and an N crossover occurred during past one or more menstrual cycles, based on the short-term and long-term moving averages calculated based on short-term and long term lengths determined to be parameters for the temperature-based prediction method. The temperature-based predictor 149 then calculates the average value of the numbers of days each between the occurrence date of a P crossover and the occurrence date of a subsequent N crossover inclusive to be an estimated high-temperature phase length (Step S24).

Subsequently, the system controller 14 obtains today's date as a registration date. The system controller 14 then generates parameter information including the target woman's user ID, the registration date, the parameters determined in the cycle-based parameter determination process and in the temperature-based parameter determination process, the predicted menstrual date determined by the cycle-based prediction method, and the estimated high-temperature phase length. After that, the system controller 14 stores the generated parameter information in the parameter DB 12*d* (Step S25) and terminates the parameter determination process.

Figure 15:
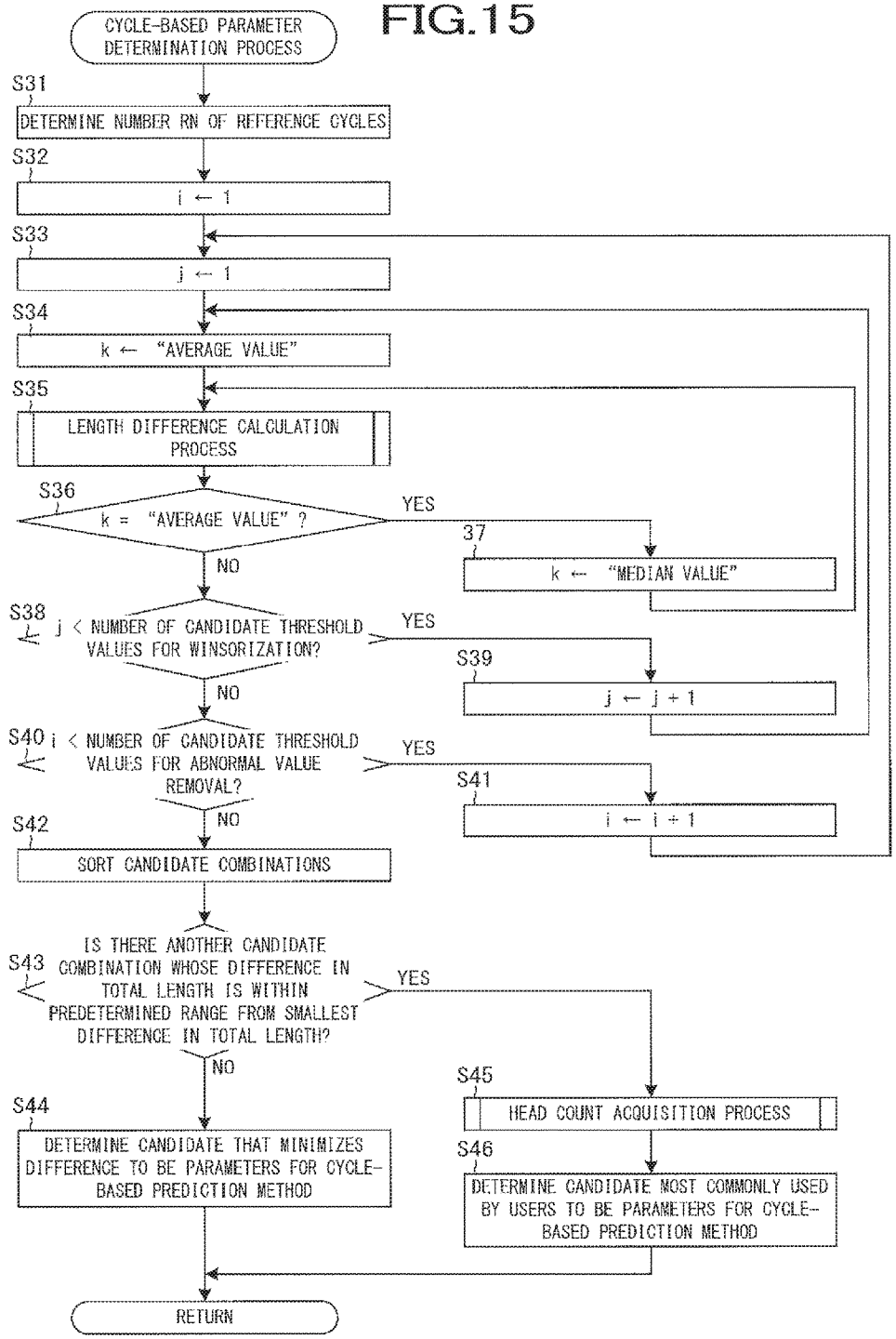
FIG. 15 is a flowchart showing an example of a cycle-based parameter determination process in the system controller 14 of the information processing server 1 according to an embodiment.

FIG. 15 is a flowchart showing an example of the cycle-based parameter determination process in the system controller 14 of the information processing server 1 according to this embodiment. As shown in FIG. 15, the candidate parameter obtainer 141 determines the number RN of reference cycles (Step S31). For example, the candidate parameter obtainer 141 obtains the initial value of the number of reference cycles prestored in the storage unit 12. The candidate parameter obtainer 141 then determines whether the number of past menstrual cycles is greater than the initial value. If the number of past menstrual cycles is greater than the initial value, the candidate parameter obtainer 141 determines the initial value to be RN. On the other hand, if the number of past menstrual cycles is less than or equal to the initial value, the candidate parameter obtainer 141 subtracts 1 from the number of past menstrual cycles to calculate RN.

Subsequently, the candidate parameter obtainer 141 sets a variable i to 1 (Step S32). The candidate parameter obtainer 141 then retrieves a candidate threshold value OF (i) for abnormal value removal from the storage unit 12. Next, the candidate parameter obtainer 141 sets a variable j to 1 (Step S33). The candidate parameter obtainer 141 then retrieves a candidate threshold value WN(j) for winsorization from the storage unit 12. Next, the candidate parameter obtainer 141 sets a representative value type k to "average value" (Step S34). After that, the system controller 14 performs a length difference calculation process (Step S35). In the length difference calculation process, the system controller 14 modifies a plurality of reference cycles, based on a combination of candidate parameters determined in Steps S32 to S34. The system controller 14 then calculates the difference between a representative value of the modified reference cycles and a base cycle to be a difference in total length. The length difference calculation process will be described in detail later.

Subsequently, the candidate parameter obtainer 141 determines whether the representative value type k is "average value" (Step S36). If the candidate parameter obtainer 141 determines that the representative value type k is "average value" (YES in Step S36), the cycle-based parameter determination process proceeds to Step S37. In Step S37, the candidate parameter obtainer 141 changes the representative value type k to "median value", and then causes the cycle-based parameter determination process to proceed to Step S35. On the other hand, if the candidate parameter obtainer 141 determines that the representative value type k is not "average value" (NO in Step S36), the cycle-based parameter determination process proceeds to Step S38. In Step S38, the candidate parameter obtainer 141 determines whether the variable j is less than the number of candidate threshold values for winsorization. If the candidate parameter obtainer 141 determines that the number j is less than the number of candidate threshold values for winsorization (YES in Step S38), the cycle-based parameter determination process proceeds to Step S39. In Step S39, the candidate parameter obtainer 141 adds 1 to the variable j, and then causes the cycle-based parameter determination process to proceed to Step S34. On the other hand, if the candidate parameter obtainer 141 determines that the parameter number j is not less than the number of candidate threshold values for winsorization (NO in Step S38), the cycle-based parameter determination process proceeds to Step S40. In Step S40, the candidate parameter obtainer 141 determines whether the variable i is less than the number of candidate threshold values for abnormal value removal. If the candidate parameter obtainer 141 determines that the number i is less than the number of candidate threshold values for abnormal value removal (YES in Step S40), the cycle-based parameter determination process proceeds to Step S41. In Step S41, the candidate parameter obtainer 141 adds 1 to the variable i, and then causes the cycle-based parameter determination process to proceed to Step S33. On the other hand, if the candidate parameter obtainer 141 determines that the parameter number i is not less than the number of candidate threshold values for abnormal value removal (NO in Step S40), the cycle-based parameter determination process proceeds to Step S42.

In Step S42, the parameter determiner 145 sorts all the candidate combinations in ascending order of the differences in total length. Subsequently, the parameter determiner 145 identifies a candidate combination that minimizes the difference in total length as a first candidate. The parameter determiner 145 then determines whether there is another candidate combination whose difference in total length is calculated to be within a predetermined range from the difference in total length of the first candidate (Step S43). For example, the parameter determiner 145 multiplies the difference in total length of the first candidate by a coefficient prestored in the storage unit 12 to calculate a reference value for the difference in total length. The value of this coefficient is, for example, greater than 1. Next, the parameter determiner 145 determines whether there are one or more candidate combinations whose difference in total length is less than or equal to the reference value, except the first candidate. If there are one or more candidate combinations whose difference in total length is less than or equal to the reference value, the parameter determiner 145 determines that there is another candidate combination whose difference in total length is calculated to be within the predetermined range from the difference in total length of the first candidate (YES in Step S43). In this case, the parameter determiner 145 identifies candidate combination(s) that makes the difference in total length less than or equal to the reference value as second candidate(s). The parameter determiner 145 then causes the cycle-based parameter determination process to proceed to Step S45. On the other hand, if there is no candidate combination whose difference in total length is less than or equal to the reference value, the parameter determiner 145 determines that there is no other candidate combination whose difference in total length is calculated to be within the predetermined range from the difference in total length of the first candidate (NO in Step S43). In this case, the parameter determiner 145 causes the cycle-based parameter determination process to proceed to Step S44.

In Step S44, the parameter determiner 145 determines the first candidate to be parameters used in the cycle-based prediction method, and then terminates the cycle-based parameter determination process.

In Step S45, the parameter determiner 145 performs a head count acquisition process. In the head count acquisition process, the parameter determiner 145 obtains the number of users for whom the first candidate has been determined to be parameters for the cycle-based prediction method and also obtains the number of users for whom a second candidate has been determined. The head count acquisition process will be described in detail later. After that, the parameter determiner 145 determines a candidate that has been most commonly determined to be parameters for users, among the first candidate and the second candidate(s), to be parameters used in the cycle-based prediction method (Step S46), and then terminates the cycle-based parameter determination process.

Figure 16:
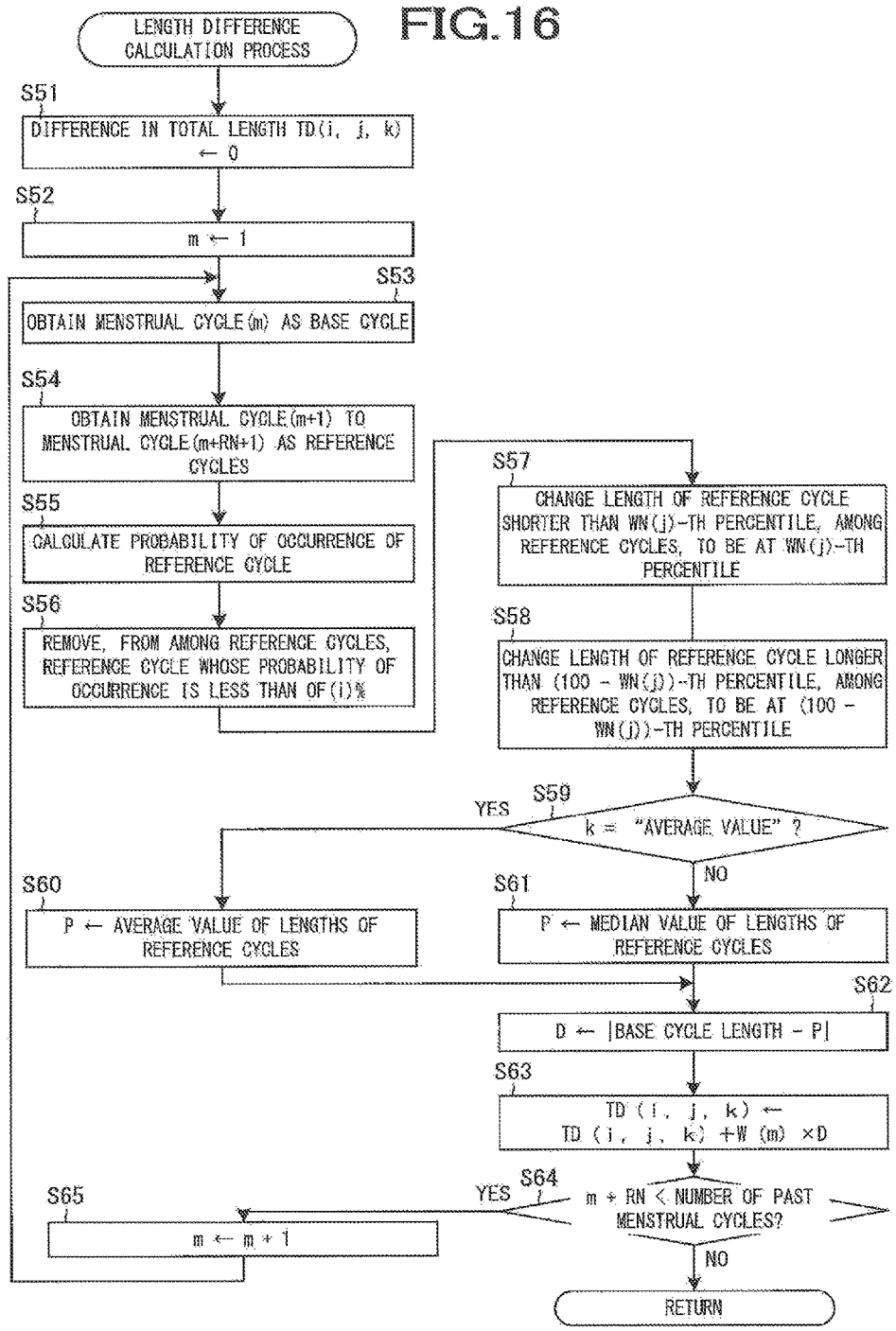
FIG. 16 is a flowchart showing an example of a length difference calculation process in the system controller 14 of the information processing server 1 according to an embodiment.

FIG. 16 is a flowchart showing an example of the length difference calculation process in the system controller 14 of the information processing server 1 according to this embodiment. As shown in FIG. 16, the parameter determiner 145 sets a difference in total length TD(i, j, k) to 0 (Step S51). Subsequently, the cycle set obtainer 142 sets a variable m for menstrual cycles to 1 (Step S52). The cycle set obtainer 142 then obtains the length of a menstrual cycle(m), among the plurality of past menstrual cycles identified in the menstrual date prediction process, as the length of a base cycle (Step S53). The menstrual cycle (m) is the m-th latest of the past menstrual cycles. Next, the cycle set obtainer 142 obtains the length of a menstrual cycle(m+1) to the length of a menstrual cycle (m+RN+1), among the past menstrual cycles identified in the menstrual date prediction process, as the lengths of reference cycles (Step S54). The cycle set obtainer 142 then sorts the obtained length of the reference cycles in ascending order.

After that, the modified reference cycle obtainer 143 counts, for each length, the number of occurrences of a reference cycle having the length. A modified reference cycle obtainer 143 then divides each number of occurrences by RN to calculate, for each length, the probability of occurrence of a reference cycle having the length (Step S55). Subsequently, the modified reference cycle obtainer 143 removes, from among the obtained lengths of the reference cycles, a reference cycle having a length whose probability of occurrence is less than OF(i) % as an abnormal value (Step S56).

Next, the modified reference cycle obtainer 143 determines the WN(j)-th percentile and the (100−WN(j))-th percentile among the lengths of the remaining reference cycles after removal of the abnormal value. The modified reference cycle obtainer 143 then changes the lengths of reference cycles shorter than the WN(j)-th percentile, among the remaining reference cycles, to be at the WN(j)-th percentile (Step S57). The modified reference cycle obtainer 143 also changes the lengths of reference cycles longer than the (100−WN(j))-th percentile, among the remaining reference cycles, to be at the (100−WN(j))-th percentile (Step S58).

After that, the representative value obtainer 144 determines whether the representative value type k is "average value" (Step S59). If the representative value obtainer 144 determines that the representative value type k is "average value" (YES in Step S59), the length difference calculation process proceeds to Step S60. In Step S60, the representative value obtainer 144 calculates the average value of the lengths of the modified reference cycles to be a representative value P, and then causes the length difference calculation process to proceed to Step S62. On the other hand, if the representative value obtainer 144 determines that the representative value type k is not "average value" (NO in Step S59), the length difference calculation process proceeds to Step S61. In Step S61, the representative value obtainer 144 determines the median value of the lengths of the modified reference cycles to be a representative value P, and then causes the length difference calculation process to proceed to Step S62.

In Step S62, the parameter determiner 145 calculates the absolute value D of the difference between the length of the base cycle and the representative value P. Subsequently, the parameter determiner 145 retrieves a weighting factor W(m) from the storage unit 12. The larger the value of m, the smaller the value of W(m). Next, the parameter determiner 145 multiplies the absolute value D of the difference by W(m) to calculate a weighted difference. The parameter determiner 145 adds the weighted difference to a difference in total length TD(i, j, k) to update the difference in total length T(i, j, k)(Step S63).

After that, the cycle set obtainer 142 determines whether the sum of the variable m and the number RN of reference cycles is less than the number of past menstrual cycles (Step S64). If the cycle set obtainer 142 determines that the sum of the variable m and the number RN of reference cycles is less than the number of past menstrual cycles (YES in Step S64), the length difference calculation process proceeds to Step S65. In Step S65, the cycle set obtainer 142 adds 1 to the variable m, and then causes the length difference calculation process to proceed to Step S53. On the other hand, if it determines that the sum of the variable m and the number RN of reference cycles is not less than the number of past menstrual cycles (NO in Step S64), the cycle set obtainer 142 terminates the length difference calculation process.

Figure 17:
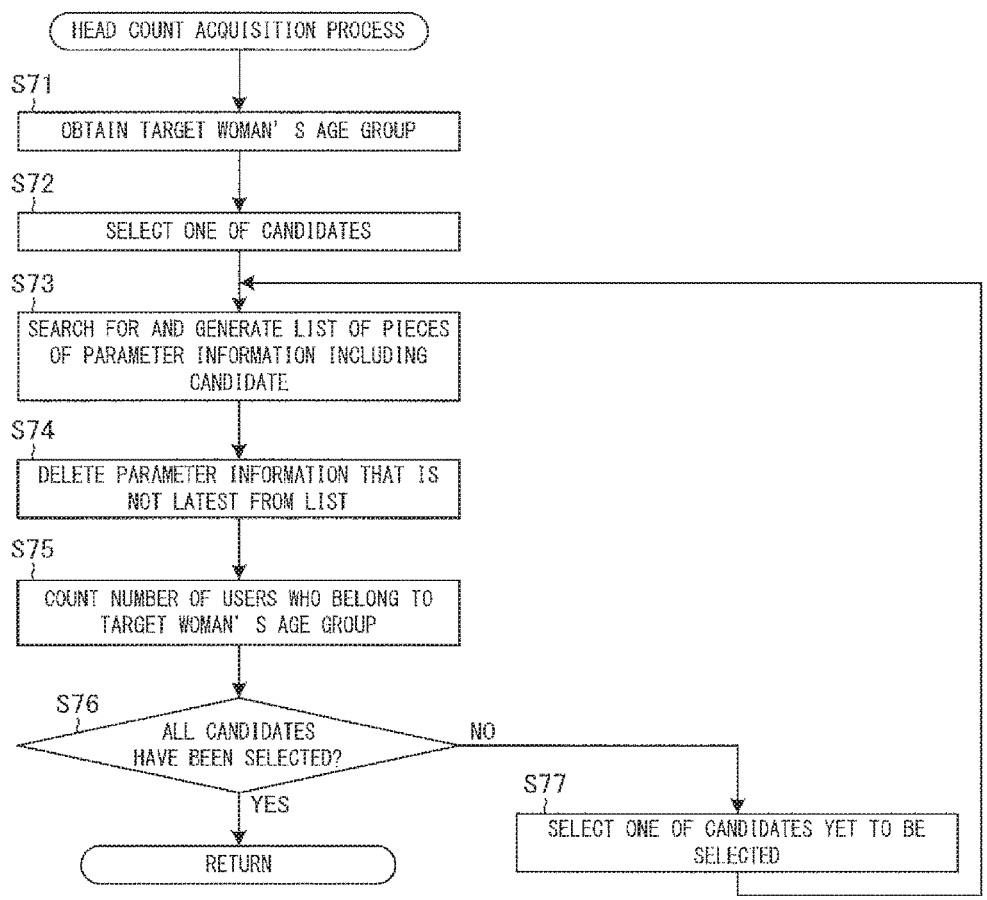
FIG. 17 is a flowchart showing an example of a head count acquisition process in the system controller 14 of the information processing server 1 according to an embodiment.

FIG. 17 is a flowchart showing an example of the head count acquisition process in the system controller 14 of the information processing server 1 according to this embodiment. The following describes an example of determining the identity of the target woman's characteristics using her age group. As shown in FIG. 17, the parameter determiner 145 retrieves the age corresponding to the target woman's user ID from the member information DB 12a. Based on the retrieved age, the parameter determiner 145 obtains the target woman's age group (Step S71). Subsequently, the parameter determiner 145 selects one of the first and one or more second candidates (Step S72). Next, the parameter determiner 145 searches the parameter DB 12d for parameter information including all the threshold value for abnormal value removal, the threshold value for winsorization, and the representative value type of the selected candidate. The parameter determiner 145 then generates a list of pieces of parameter information found by the search (Step S73).

After that, the parameter determiner 145 deletes parameter information that is not the latest from the list (Step S74). For example, the parameter determiner 145 obtains a user ID from parameter information in the list. The system controller 14 then searches the parameter DB 12d for parameter information that includes the latest registration date among the pieces of parameter information corresponding to the obtained user ID. Subsequently, the parameter determiner 145 deletes parameter information stored before the latest registration date from the list. The parameter determiner 145 performs these for each of the piece of parameter information in the list.

Next, the parameter determiner 145 counts the number of users who belong to the target woman's age group (Step S75). For example, the parameter determiner 145 retrieves, from the member information DB 12a, the age corresponding to a user ID included in parameter information in the list. Based on the retrieved age, the parameter determiner 145 obtains the age group of the user indicated by the user ID. If the obtained age group is the same as the target woman's age group, the parameter determiner 145 increases by one the number of users. The parameter determiner 145 performs these for each of the piece of parameter information in the list (Step S75).

After that, the parameter determiner 145 determines whether all the first and one or more second candidates have been selected (Step S76). If the parameter determiner 145 determines that some of the candidates remain to be selected (YES in Step S76), the head count acquisition process proceeds to Step S77. In Step S77, the parameter determiner 145 selects one of the candidates yet to be selected, and then causes the head count acquisition process to proceed to Step S73. On the other hand, if it determines that all the candidates have been selected (YES in Step S76), the parameter determiner 145 terminates the head count acquisition process.

Figure 18:
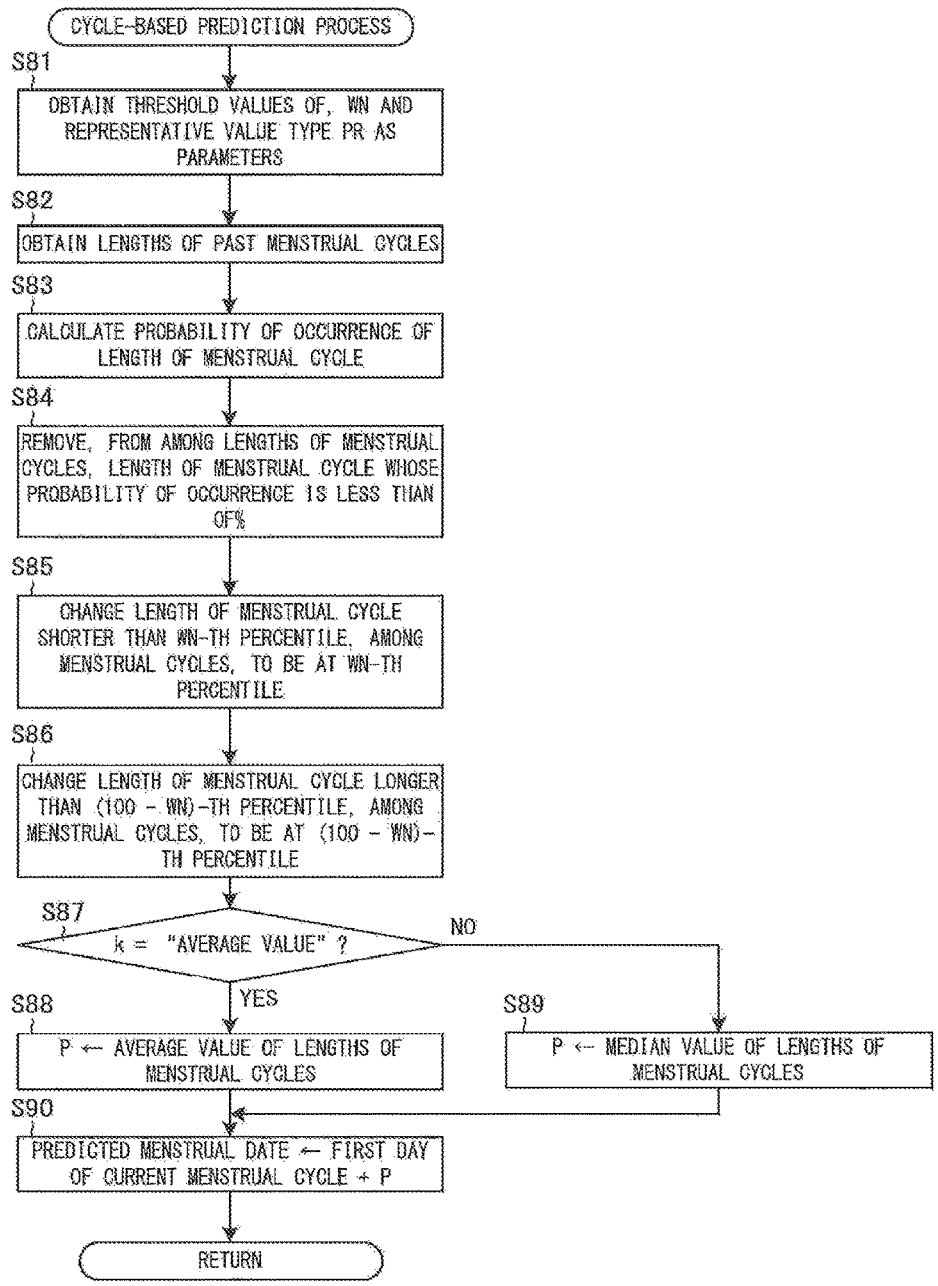
FIG. 18 is a flowchart showing an example of a cycle-based prediction process in the system controller 14 of the information processing server 1 according to an embodiment.

FIG. 18 is a flowchart showing an example of the cycle-based prediction process in the system controller 14 of the information processing server 1 according to this embodiment. As shown in FIG. 18, the cycle-based predictor 146 obtains the threshold value OF for abnormal value removal, the threshold value WN for winsorization, and a representative value type PR determined to be parameters (Step S81). The cycle-based predictor 146 then obtains the lengths of the target woman's past menstrual cycles (Step S82).

Subsequently, the cycle-based predictor 146 counts, for each length, the number of occurrences of a past menstrual cycle having the length. The cycle-based predictor 146 then divides each number of occurrences by the number of the past menstrual cycles to calculate, for each length, the probability of occurrence of a past menstrual cycle having the length (Step S83). Next, the cycle-based predictor 146 removes, from among the obtained lengths of the menstrual cycles, a menstrual cycle having a length whose probability of occurrence is less than OF % as an abnormal value (Step S84). After that, the cycle-based predictor 146 determines the WN-th percentile and the (100−WN)-th percentile among the lengths of the remaining menstrual cycles after removal of the abnormal value. The cycle-based predictor 1464 then changes the lengths of menstrual cycles shorter than the WN-th percentile, among the remaining menstrual cycles, to be at the WN-th percentile (Step S85). The cycle-based predictor 146 also changes the lengths of menstrual cycles longer than the (100−WN)-th percentile, among the remaining menstrual cycles, to be at the (100−WN)-th percentile (Step S86).

Subsequently, the cycle-based predictor 146 determines whether the representative value type PR is "average value" (Step S87). If the cycle-based predictor 146 determines that the representative value type PR is "average value" (YES in Step S87), the cycle-based prediction process proceeds to Step S88. In Step S88, the cycle-based predictor 146 calculates the average value of the lengths of the modified menstrual cycles to be a representative value P, and then causes the cycle-based prediction process to proceed to Step S90. On the other hand, if the cycle-based predictor 146 determines that the representative value type PR is not "average value" (NO in Step S87), the cycle-based prediction process proceeds to Step S89. In Step S89, the cycle-based predictor 146 determines the median value of the lengths of the modified menstrual cycles to be a representative value P, and then causes the cycle-based prediction process to proceed to Step S90.

In Step S90, the cycle-based predictor 146 adds the representative value P to the date of the first day of the current menstrual cycle, to calculate a predicted menstrual date. The cycle-based predictor 146 then terminates the cycle-based prediction process.

Figure 19:
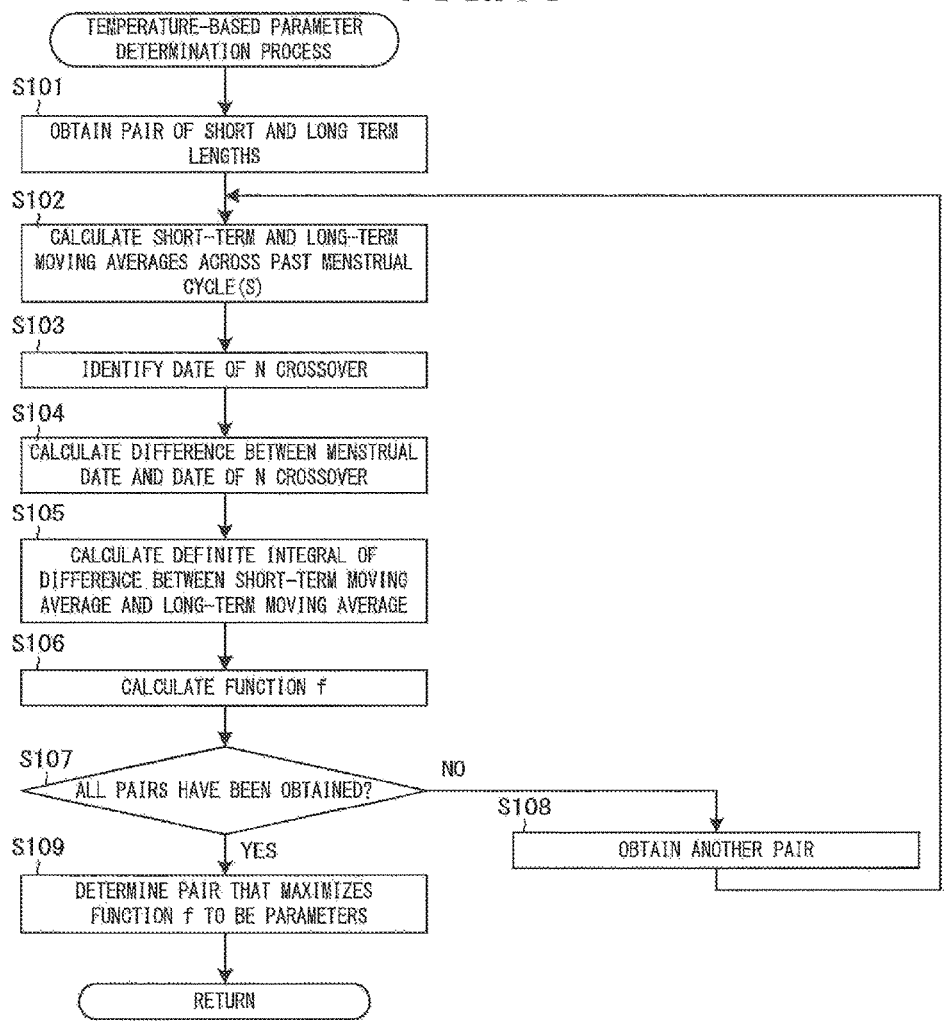
FIG. 19 is a flowchart showing an example of a temperature-based parameter determination process in the system controller 14 of the information processing server 1 according to an embodiment.

FIG. 19 is a flowchart showing an example of the temperature-based parameter determination process in the system controller 14 of the information processing server 1 according to this embodiment. As shown in FIG. 19, the period length determiner 147 obtains a pair of short and longterm lengths (Step S101). Based on the obtained pair and on the target woman's body temperatures actually measured during the past one or more menstrual cycles, the period length determiner 147 calculates short-term and long-term moving averages of the body temperatures across the past one or more menstrual cycles (Step S102). The period length determiner 147 then identifies the occurrence date of an N crossover, based on the calculated moving averages (Step S103). The occurrence date of a P crossover is identified in the same manner as the occurrence date of the N crossover except that the vertical relationship between the short-term moving average and the long-term moving average is reversed. How to identify the occurrence date of a P crossover is mentioned in the description of Step S9 of the menstrual date prediction process shown in FIG. 13.

Subsequently, the period length determiner 147 calculates the difference between a menstrual date that is the day after the last day of each of the past one or more menstrual cycles and the occurrence date of a P crossover nearest to the menstrual date. The period length determiner 147 then calculates the average value of differences each of which is the difference between a menstrual date and the occurrence date of the corresponding P crossover (Step S104). That is, the period length determiner 147 calculates Equation 3. Next, the period length determiner 147 calculates the definite integral of the difference between the short-term moving average and the long-term moving average across the past one or more menstrual cycles (Step S105). That is, the period length determiner 147 calculates Equation 5. After that, the period length determiner 147 calculates the function f expressed as Equation 6, using the results of the calculations made in Steps S104 and S105.

Subsequently, the period length determiner 147 determines whether it has obtained all pairs of short and long term lengths (Step S107). If the period length determiner 147 determines that some of the pairs remain to be obtained (NO in Step S107), the temperature-based parameter determination process proceeds to Step S108. In Step S108, the period length determiner 147 obtains one of the pairs yet to be obtained, and then causes the temperature-based parameter determination process to proceed to Step S102. On the other hand, if the period length determiner 147 determines that it has obtained all the pairs (YES in Step S107), the temperature-based parameter determination process proceeds to Step S109.

In Step S109, the period length determiner 147 determines a pair that maximizes the function f, among the pairs of short and long term lengths, to be parameters for the temperature-based prediction method. The temperature-based predictor 149 then terminates the temperature-based parameter determination process.

As described above, according to this embodiment, the system controller 14 may obtain at least either a plurality of candidate threshold values for abnormal value removal or a plurality of candidate threshold values for winsorization. The system controller 14 may also obtain a base cycle and a plurality of reference cycles from among a target woman's plurality of past menstrual cycles. The system controller 14 may also obtain, for each candidate threshold value, a plurality of reference cycles modified by applying predetermined processing to an outlier identified using the candidate threshold value, among the reference cycles. The system controller 14 may also obtain, for each candidate threshold value, a representative value of the modified reference cycles. The system controller 14 may also compare the base cycle with the representative value obtained for each candidate threshold value. Based on the result of the comparison, the system controller 14 may determine a threshold value used to predict the length of the target woman's menstrual cycle, from among the candidate threshold values. In this case, the system controller 14 can determine a threshold value that prevents a decrease in the accuracy of the prediction, even if there is a large variation in her menstrual cycle. Consequently, based on this threshold value, the system controller 14 can predict her menstrual cycle while preventing a decrease in the accuracy of the prediction and can predict her menstrual date using this menstrual cycle.

The system controller 14 may obtain a plurality of candidate threshold values for abnormal value removal or a plurality of candidate threshold values for winsorization. The system controller 14 may also obtain, for each candidate combination including a candidate threshold value for abnormal value removal and a candidate threshold value for winsorization, a plurality of reference cycles modified by removing a reference cycle identified as an abnormal value based on the threshold value for abnormal value removal from among original reference cycles and also by changing the length of a reference cycle identified as an outlier based on the threshold value for winsorization, among the original reference cycles left after removal of the abnormal value, to a length corresponding to the threshold value for winsorization. The system controller 14 may also obtain, for each candidate combination, a representative value of the modified reference cycles. The system controller 14 may also compare, for each candidate combination, the base cycle with the corresponding representative value. Based on the result of the comparison, the system controller 14 may determine a candidate combination used for the prediction, from among the candidate combinations. In this case, the system controller 14 can determine a threshold value for abnormal value removal and a threshold value for winsorization that prevent a decrease in the accuracy of the prediction, even if there is a large variation in her menstrual cycle.

The system controller 14 may obtain a threshold value for abnormal value removal or a threshold value for winsorization. The system controller 14 may also remove, from among the menstrual cycles, a menstrual cycle identified as an abnormal value based on the threshold value for abnormal value removal. The system controller 14 may also change the length of a menstrual cycle identified as an outlier based on the threshold value for winsorization, among the menstrual cycles left after removal of the abnormal value, to a length corresponding to the threshold value for winsorization. The system controller 14 may then predict the length of the target woman's menstrual cycle, based on the menstrual cycles including the menstrual cycle changed in length. In this case, the system controller 14 can predict her menstrual cycle while preventing a decrease in the accuracy of the prediction and can predict her menstrual date using this menstrual cycle, even if there is a large variation in her menstrual cycle.

The system controller 14 may obtain a plurality of cycle sets. The system controller 14 may also obtain, for each candidate of a candidate threshold value and a cycle set, a plurality of modified reference cycles. The system controller 14 may also obtain, for each candidate of a candidate threshold value and a cycle set, a representative value of the modified reference cycles. The system controller 14 may also compare, for each candidate of a candidate threshold value and a cycle set, the base cycle with the corresponding representative value. Based on a plurality of comparison results obtained for each candidate threshold value, the system controller 14 may determine a threshold value used for the prediction. In this case, the system controller 14 can determine a more appropriate threshold value.

The system controller 14 may obtain a plurality of continuous reference cycles and a base cycle that is continuous with the reference cycles and newer than the reference cycles. The system controller 14 may also determine a threshold value used for the prediction by weighting the comparison result obtained for each candidate threshold value. The older the base cycle is, the less weight the system controller 14 may assign to the result of the comparison between the base cycle and the representative value. In this case, the system controller 14 can determine a more appropriate threshold value used to predict her menstrual cycle.

A first candidate minimizes the difference between the representative value and the base cycle. When there is a second candidate for which a difference within a predetermined range from the difference obtained for the first candidate is obtained among the candidate threshold values, the system controller may determine a threshold value used for the prediction from among the first and second candidates, based on the number of users for whom the first candidate has been determined to be a threshold value used for the prediction and on the number of users for whom the second candidate has been determined to be a threshold value used for the prediction, among users except the target woman. In this case, the system controller 14 can determine a more appropriate threshold value used to predict her menstrual cycle.

The system controller 14 may determine a threshold value used for the prediction, based on the number of users for whom the first candidate has been determined to be a threshold value used for the prediction and who have the same type of characteristics as the target woman and on the number of users for whom the second candidate has been determined to be a threshold value used for the prediction and who have the same type of characteristics as the target woman. In this case, the system controller 14 can determine a threshold value more appropriate for the target woman.

The system controller 14 may obtain, for each candidate threshold value, both the average value and the median value of the modified reference cycles. The system controller 14 may also compare, for each candidate threshold value, the base cycle both with the corresponding average value and with the corresponding median value. The system controller 14 may then determine a candidate combination used for the prediction, from among a plurality of candidate combinations each including a candidate threshold value and a representative value type. In this case, the system controller 14 can obtain a representative value appropriate to the distribution of the target woman's past menstrual cycles.

If the timing at which a short-term moving average of her body temperatures measured during the target woman's current menstrual cycle exceeds a corresponding long-term moving average has not yet come during the current menstrual cycle, the system controller 14 may predict the length of her current menstrual cycle, based on the determined threshold value and the target woman's past menstrual cycles, and predict her next menstrual date, based on the predicted length. If the timing at which the short-term moving average exceeds the long-term moving average has come during the current menstrual cycle, the system controller 14 may predict her next menstrual date, based on the timing. In this case, the system controller 14 can predict her menstrual date more accurately after the transition from the low-temperature phase to the high-temperature phase.

The system controller 14 may determine a short term length and a long term length so that timing (s) at which a short-term moving average calculated with the short term length falls below a long-term moving average calculated with the long term length, of a plurality of days of her body temperatures measured during the past one or more menstrual cycles, coincides with past one or more menstrual dates. The system controller 14 may identify the timing at which a moving average with the short term length exceeds a moving average with the long term length, of her body temperatures measured during a target menstrual cycle. Based on the identified timing, the system controller 14 may predict her next menstrual date during the target menstrual cycle or estimate the arrival of her ovulation date during the target menstrual cycle. In this case, the moving averages smooth time-series body temperature. Thus, by identifying this timing, even if the body temperature fluctuates before and after the timing of the actual transition from a low-temperature phase to a high-temperature phase, the timing can be correctly identified. A menstrual date comes at the timing of the transition from a low-temperature phase to a subsequent high-temperature phase. Thus, the system controller 14 can appropriately determine a short term length and a long term length. This can prevent a decrease in the accuracy of at least either estimating her ovulation date or predicting her menstrual date.

The system controller 14 may predict her next menstrual date by adding a representative value of the numbers of days each between a timing at which the short-term moving average calculated with the short term length exceeds the long-term moving average calculated with the long term length and a subsequent timing at which the short-term moving average calculated with the short term length falls below the long-term moving average calculated with the long term length, during the past one or more menstrual cycles, to the timing at which the short-term moving average calculated with the short term length exceeds the long-term moving average with calculated the long term length during the current menstrual cycle. In this case, the system controller 14 can perform at least either estimation of her ovulation date or prediction of her menstrual date, more appropriately based on the tendency of the target woman's high-temperature phase.

The system controller 14 may determine the short term length and the long term length so that the time difference between her menstrual date and a timing at which a short-term moving average of her body temperatures measured during the past one or more menstrual cycles falls below a long-term moving average of the body temperatures is small, and also so that the value of integral of the difference between the short-term moving average and the long-term moving average across the past one or more menstrual cycles is large. In this case, the system controller 14 can determine more appropriate short and long term lengths, based on the value of integral of the difference between the short-term and the long-term moving averages of the body temperatures and on the time difference between the menstrual date and the timing at which the short-term moving average of the body temperatures falls below the long-term moving average.

If the timing at which the short-term moving average exceeds the long-term moving average during the current menstrual cycle is not identified, the system controller 14 may predict her next menstrual date, based on the lengths of the past one or more menstrual cycles. In this case, even when the transition from the low-temperature phase to the high-temperature phase has not yet occurred, the system controller 14 can predict her menstrual date.

In each embodiment described above, an information processing device according to the present invention is embodied in a server device in a client-server system. However, the information processing device according to the present invention may be embodied in an information processing device except the server device. For example, the information processing device according to the present invention may be embodied in the user terminal 2. In this case, the information processing device may receive actually measured body temperatures and a menstrual date entered by a user and then estimate the user's ovulation date or predict her next menstrual date.

REFERENCE SIGNS LIST

1 information processing server
2 user terminal
11 communication unit
12 storage unit
12*a* member information DB
12*b* body temperature DB
12*c* menstrual date DB
12*d* parameter DB
13 input/output interface
14 system controller
14*a* CPU
14*b* ROM
14*c* RAM
15 system bus
141 candidate parameter obtainer
142 cycle set obtainer
143 modified reference cycle obtainer
144 representative value obtainer
145 parameter determiner
146 cycle-based predictor
147 period length determiner
148 timing identification unit
149 temperature-based predictor
NW network
S information processing system

The invention claimed is:

1. A computer architecture comprising: at least one memory configured to store computer program code; and at least one processor configured to access said computer program code and operate as instructed by said computer program code, said computer program code configured to cause at least one of said at least one processor to: determine, based on a plurality of days of first body temperatures measured during past one or more menstrual cycles, a short term length and a long term length such that one or more timings at which a first short-term moving average crosses over a first long-term moving average to be lower than the first long term moving average coincides with known past one or more menstrual dates, wherein the first short-term moving average is calculated based on the short term length and the plurality of days of first body temperatures, and wherein the first long-term moving average is calculated based on the long term length and the plurality of days of first body temperatures, identify a timing at which a second short-term moving average crosses over a second long-term moving average to be higher than the second long-term moving average, wherein the second short-term moving average is calculated based on the determined short term length and a plurality of days of second body temperatures measured during a target menstrual cycle, and wherein the second long-term moving average is calculated based on the determined long term length and the plurality of days of second body temperatures, and predict a next menstrual date during the target menstrual cycle or estimate arrival of an ovulation date during the target menstrual cycle, based on the identified timing.

2. The computer architecture according to claim 1, wherein the computer program code is further configured to cause at least one of said at least one processor to predict the next menstrual date by adding a representative value of the numbers of days each between a timing at which the second short-term moving average exceeds the second long-term moving average and a timing at which the second short-term moving average falls below the second long-term moving average, during the past one or more menstrual cycles, to the identified timing.

3. The computer architecture according to claim 1, wherein the computer program code is further configured to cause at least one of said at least one processor to determine the short term length and the long term length so that a time difference between a menstrual date and a timing at which the first short-term moving average of body temperatures measured during the past one or more menstrual cycles falls below the first long-term moving average of the body temperatures is small, and also so that a value of integral of a difference between the first short-term moving average and the first long-term moving average across the past one or more menstrual cycles is large.

4. The computer architecture according to claim 1, wherein the computer program code is further configured to cause at least one of said at least one processor to output the predicted next menstrual date or the estimated ovulation date.

5. An information processing method performed by a computer, the method comprising: determining, based on a plurality of days of first body temperatures measured during past one or more menstrual cycles, a short term length and a long term length such that one or more timings at which a first short-term moving average crosses over a first long-term moving average to be lower than the first long term moving average coincides with known past one or more menstrual dates, wherein the first short-term moving average is calculated based on the short term length and the plurality of days of first body temperatures, and wherein the first long-term moving average is calculated based on the long term length and the plurality of days of first body temperatures; identifying a timing at which a second short-term moving average crosses over a second long-term moving average to be higher than the second long-term moving average, wherein the second short-term moving average is calculated based on the determined short term length and a plurality of days of second body temperatures measured during a target menstrual cycle, and wherein the second long-term moving average is calculated based on the determined long term length and the plurality of days of second body temperatures; and predicting a next menstrual date during the target menstrual cycle or estimating arrival of an ovulation date during the target menstrual cycle, based on the identified timing.

6. A non-transitory computer readable medium storing thereon an information processing program, the information processing program causing a computer to: determine, based on a plurality of days of first body temperatures measured during past one or more menstrual cycles, a short term length and a long term length such that one or more timings at which a first short-term moving average crosses over a first long-term moving average to be lower than the first long term moving average coincides with known past one or more menstrual dates, wherein the first short-term moving average is calculated based on the short term length and the plurality of days of first body temperatures, and wherein the first long-term moving average is calculated based on the long term length and the plurality of days of first body temperatures; identify a timing at which a second short-term moving average crosses over a second long-term moving average to be higher than the second long-term moving average, wherein the second short-term moving average is calculated based on the determined short term length and a plurality of days of second body temperatures measured during a target menstrual cycle, and wherein the second long-term moving average is calculated based on the determined long term length and the plurality of days of second body temperatures; and predict a next menstrual date during the target menstrual cycle or estimate arrival of an ovulation date during the target menstrual cycle, based on the identified timing.

* * * * *